(12) United States Patent
Okabe

(10) Patent No.: US 9,025,848 B2
(45) Date of Patent: May 5, 2015

(54) X-RAY CT APPARATUS AND CONTROL METHOD FOR RECONSTRUCTING X-RAY CT IMAGES FROM FILTERED PROJECTION DATA

(75) Inventor: Masakazu Okabe, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 232 days.

(21) Appl. No.: 13/703,448

(22) PCT Filed: Jun. 16, 2011

(86) PCT No.: PCT/JP2011/063766
§ 371 (c)(1),
(2), (4) Date: Dec. 11, 2012

(87) PCT Pub. No.: WO2011/158893
PCT Pub. Date: Dec. 22, 2011

(65) Prior Publication Data
US 2013/0094739 A1  Apr. 18, 2013

(30) Foreign Application Priority Data
Jun. 17, 2010  (JP) ................................. 2010-138576

(51) Int. Cl.
*G06K 9/00* (2006.01)
*G01N 23/04* (2006.01)
(Continued)

(52) U.S. Cl.
CPC .............. *G01N 23/046* (2013.01); *A61B 6/032* (2013.01); *A61B 6/5205* (2013.01); *G06T 11/006* (2013.01); *G06T 2211/421* (2013.01); *A61B 6/5258* (2013.01); *Y10S 378/901* (2013.01)

(58) Field of Classification Search
None
See application file for complete search history.

(56) References Cited

U.S. PATENT DOCUMENTS 7,684,539 B2 *  3/2010  Goto et al. ........................ 378/15
8,045,776 B2 * 10/2011  Hopkins et al. ............... 382/131
(Continued)

FOREIGN PATENT DOCUMENTS

JP  2004-070793  4/2004
JP  2004-313391  11/2004
(Continued)

OTHER PUBLICATIONS

Takayuki Kamodura, Masakazu Okabe, Rika Baba, Kiyoshi Sakamoto, "FPD, Tosai C-Arm Sochi no 3D Kaikosei Kino Kojo to Kogashitsuka", Japanese Society of Radiological Technology Sokai Gakujutsu Taikai, Feb. 20, 2004, Dai 60 Kai, 581, p. 225.
(Continued)

*Primary Examiner* — Matthew Bella
*Assistant Examiner* — Jason Heidemann
(74) *Attorney, Agent, or Firm* — Brundidge & Stanger, P.C.

(57) ABSTRACT

In order to generate an X-ray CT image with optimal quality for each part and each region of an object when scanning the object across a plurality of parts using a plane detector, there is provided an X-ray CT apparatus including smoothing means 230 and filtering means 250 for generating a convolution filter on the basis of feature amounts of projection data output from the X-ray detector 12 and superimposing the convolution filter on the projection data, reconstruction means 200 for generating an X-ray CT image of the object by performing a reconstruction operation on the projection data on which the convolution filter is superimposed, and image display means 280 for displaying the image generated by the reconstruction means 200.

10 Claims, 20 Drawing Sheets

(51) Int. Cl.
*A61B 6/03* (2006.01)
*A61B 6/00* (2006.01)
*G06T 11/00* (2006.01)

(56) References Cited

U.S. PATENT DOCUMENTS

| | | | |
|---|---|---|---|
| 2002/0071600 A1* | 6/2002 | Yamada | 382/132 |
| 2004/0028265 A1* | 2/2004 | Nishide | 382/131 |
| 2006/0023831 A1* | 2/2006 | Imai et al. | 378/4 |
| 2007/0172104 A1* | 7/2007 | Nishide et al. | 382/131 |
| 2007/0230760 A1* | 10/2007 | Omi et al. | 382/131 |
| 2008/0219532 A1* | 9/2008 | Hopkins et al. | 382/131 |
| 2008/0273778 A1* | 11/2008 | Goto et al. | 382/131 |
| 2010/0054567 A1* | 3/2010 | Hillebrand et al. | 382/131 |
| 2010/0061608 A1* | 3/2010 | Galant | 382/128 |

FOREIGN PATENT DOCUMENTS

| | | |
|---|---|---|
| JP | 2005-160544 | 6/2005 |
| JP | 2006-034785 | 2/2006 |
| JP | 2007-190182 | 8/2007 |
| JP | 2008-148970 | 7/2008 |
| JP | 4348989 | 7/2009 |
| WO | 2005-110232 | 11/2005 |
| WO | 2011-158893 | 12/2011 |

OTHER PUBLICATIONS

International Search Report, International Application No. PCT/JP2011/063766, Filed Jun. 16, 2011, Mailed Aug. 30, 2011, ISA/Japenese Patent Office.

* cited by examiner

FIG. 11-1

| | 61 | | | 62 | |
|---|---|---|---|---|---|
| P(u−1,v−1) | P(u, v−1) | P(u+1,v−1) | $\dfrac{Wa \cdot Wb}{(1+2Wa)(1+2Wb)}$ | $\dfrac{Wb}{(1+2Wa)(1+2Wb)}$ | $\dfrac{Wa \cdot Wb}{(1+2Wa)(1+2Wb)}$ |
| P(u−1,v) | P(u, v) | P(u+1,v) | $\dfrac{Wa}{(1+2Wa)(1+2Wb)}$ | $\dfrac{1}{(1+2Wa)(1+2Wb)}$ | $\dfrac{Wa}{(1+2Wa)(1+2Wb)}$ |
| P(u−1,v+1) | P(u, v+1) | P(u+1,v+1) | $\dfrac{Wa \cdot Wb}{(1+2Wa)(1+2Wb)}$ | $\dfrac{Wb}{(1+2Wa)(1+2Wb)}$ | $\dfrac{Wa \cdot Wb}{(1+2Wa)(1+2Wb)}$ |

(with × between the two matrices)

FIG. 11-2

| 63 | | 64 |
|---|---|---|
| P(u,v−1) | | $\dfrac{Wb}{(1+2Wb)}$ |
| P(u, v) | × | $\dfrac{1}{(1+2Wb)}$ |
| P(u,v+1) | | $\dfrac{Wb}{(1+2Wb)}$ |

FIG. 11-3

| | 65 | | | 66 | |
|---|---|---|---|---|---|
| P(u−1,v−2) | P(u, v−2) | P(u+1,v−2) | $\dfrac{Wa \cdot Wb^2}{(1+2Wa)(1+2Wb+2Wb^2)}$ | $\dfrac{Wb^2}{(1+2Wa)(1+2Wb+2Wb^2)}$ | $\dfrac{Wa \cdot Wb^2}{(1+2Wa)(1+2Wb+2Wb^2)}$ |
| P(u−1,v−1) | P(u, v−1) | P(u+1,v−1) | $\dfrac{Wa \cdot Wb}{(1+2Wa)(1+2Wb+2Wb^2)}$ | $\dfrac{Wb}{(1+2Wa)(1+2Wb+2Wb^2)}$ | $\dfrac{Wa \cdot Wb}{(1+2Wa)(1+2Wb+2Wb^2)}$ |
| P(u−1,v) | P(u, v) | P(u+1,v) | $\dfrac{Wa}{(1+2Wa)(1+2Wb+2Wb^2)}$ | $\dfrac{1}{(1+2Wa)(1+2Wb+2Wb^2)}$ | $\dfrac{Wa}{(1+2Wa)(1+2Wb+2Wb^2)}$ |
| P(u−1,v+1) | P(u, v+1) | P(u+1,v+1) | $\dfrac{Wa \cdot Wb}{(1+2Wa)(1+2Wb+2Wb^2)}$ | $\dfrac{Wb}{(1+2Wa)(1+2Wb+2Wb^2)}$ | $\dfrac{Wa \cdot Wb}{(1+2Wa)(1+2Wb+2Wb^2)}$ |
| P(u−1,v+2) | P(u, v+2) | P(u+1,v+2) | $\dfrac{Wa \cdot Wb^2}{(1+2Wa)(1+2Wa+2Wa^2)}$ | $\dfrac{Wb^2}{(1+2Wa)(1+2Wb+2Wb^2)}$ | $\dfrac{Wa \cdot Wb^2}{(1+2Wa)(1+2Wa+2Wa^2)}$ |

×

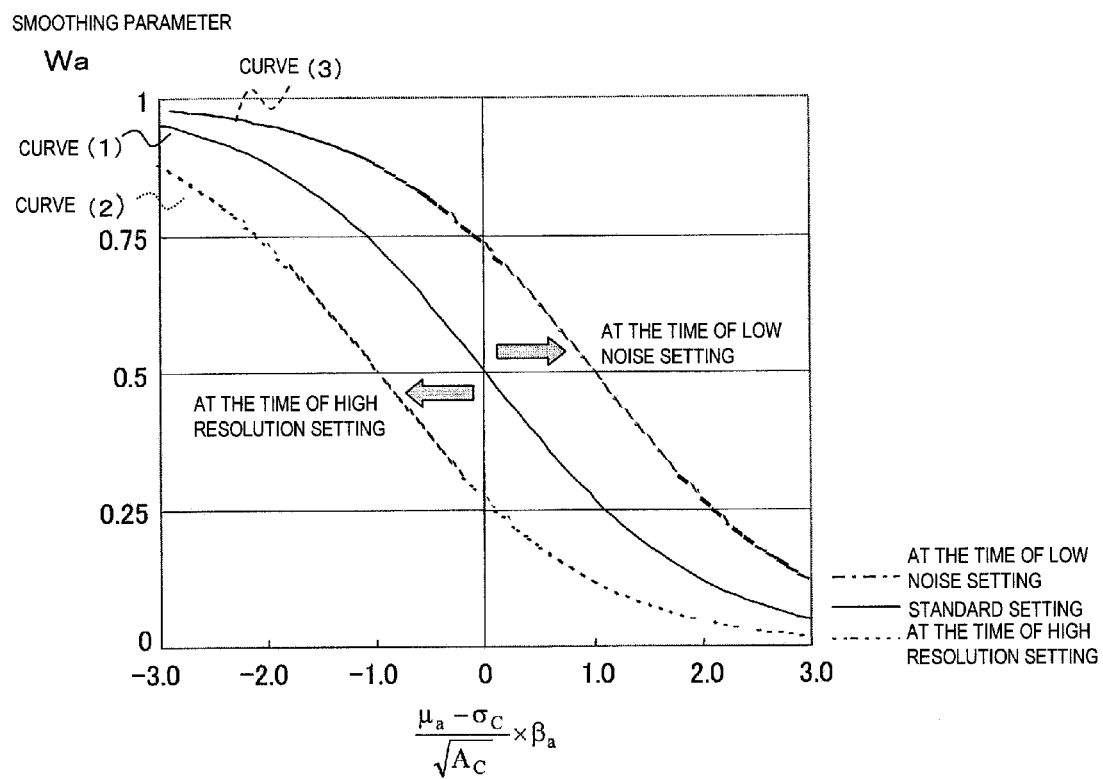

X-RAY CT APPARATUS AND CONTROL METHOD FOR RECONSTRUCTING X-RAY CT IMAGES FROM FILTERED PROJECTION DATA

TECHNICAL FIELD

The present invention relates to an X-ray CT apparatus and in particular, to an X-ray CT apparatus that generates an X-ray CT image with optimal quality for each part and each region of an object when scanning the object across a plurality of parts using a plane detector, and a control method thereof.

BACKGROUND ART

Generally, as the body thickness of a scanned part increases, the output value of an X-ray detector decreases and its error increases. For this reason, noise of an X-ray CT image reconstructed for a region with a large body thickness increases. On the other hand, in a conventional X-ray CT apparatus, an X-ray CT image of an object has usually been generated using one reconstruction filter in each CT scan. For this reason, there have been cases in which an optimal X-ray CT image can be provided for a certain part of the object but the optimal image quality is not obtained for other regions.

In such a case, there is known an X-ray CT apparatus that outputs an X-ray CT image, in which a plurality of reconstructed images are combined by calculating a plurality of reconstructed images through superimposing a plurality of reconstruction filters, such as a smoothing filter and a sharpening filter, and setting an addition coefficient corresponding to the CT value at each point for each of the reconstructed images and adding the addition coefficients (PTL 1).

CITATION LIST

Patent Literature

[PTL 1] JP-A-2006-34785

SUMMARY OF INVENTION

Technical Problem

In the X-ray CT apparatus described above, however, there is a problem in that a computation time is required because the reconstructed images are calculated for a plurality of reconstruction filters. In addition, in particular, when a flat panel detector is used as the X-ray detector, the amount of noise of imaging data is large. Accordingly, there is a problem in that a satisfactory reconstructed CT image cannot be obtained unless it is determined whether to use a smoothing filter or a sharpening filter in consideration of not only the X-ray absorption coefficient (so-called CT value) of each reconstruction point but also the quality (noise) of the reconstructed image.

In view of the above-described problems, it is an object of the present invention to provide an X-ray CT apparatus that suppresses an increase in computation time and generates an X-ray CT image with optimal quality for each part.

Solution to Problem

The present invention realizes an X-ray CT apparatus that suppresses an increase in computation time and generates an X-ray CT image with optimal quality for each part by generating an image processing filter that changes continuously on the basis of the value of projection data and performing an image reconstruction operation.

More specifically, an X-ray CT apparatus related to the present invention includes: an X-ray source that generates X-rays; an X-ray detector that is disposed opposite the X-ray source and detects the X-ray transmitted through an object to output projection data of the object; rotation means configured to rotate the X-ray source and the X-ray detector in a state where the X-ray source and the X-ray detector are disposed opposite each other; filter generation means configured to generate an image processing filter according to feature amounts of a pixel value included in the projection data; reconstruction means configured to generate an X-ray CT image of the object by performing a reconstruction operation on the projection data using the generated image processing filter; and image display means configured to display the X-ray CT image.

Advantageous Effects of Invention

According to the present invention, it is possible to provide an X-ray CT apparatus that suppresses an increase in computation time and generates an X-ray CT image with optimal quality for each region and each part of the object in cone-beam CT imaging for scanning an object across a plurality of parts using a plane detector.

For example, in cone-beam CT imaging from the chest to the abdomen, it is possible to realize an X-ray CT apparatus capable of generating an X-ray CT image with high spatial resolution in a chest region where the amount of X-ray absorption is small and generating an X-ray CT image, which has low contrast and is excellent in resolution, in an abdomen region where the amount of X-ray absorption is large and the output value of the X-ray detector is small.

BRIEF DESCRIPTION OF DRAWINGS

FIG. 1-2 is a schematic configuration diagram showing a C-arm type cone-beam X-ray CT apparatus 1a mounted in a movable X-ray apparatus to which the present invention is applied.

FIG. 2 is a block diagram showing components of filter conversion information generation means 220.

FIG. 11-1 is an explanatory view illustrating the convolution operation when the size of the convolution filter is 3×3.

FIG. 11-2 is an explanatory view illustrating the convolution operation when the size of the convolution filter is 1×3.

FIG. 11-3 is an explanatory view illustrating the convolution operation when the size of the convolution filter is 3×5.

FIG. 12 is an explanatory view showing the curves which show a function of the standard deviation σc of projection data 211 and a smoothing parameter Wa.

DESCRIPTION OF EMBODIMENTS

Figure 1:
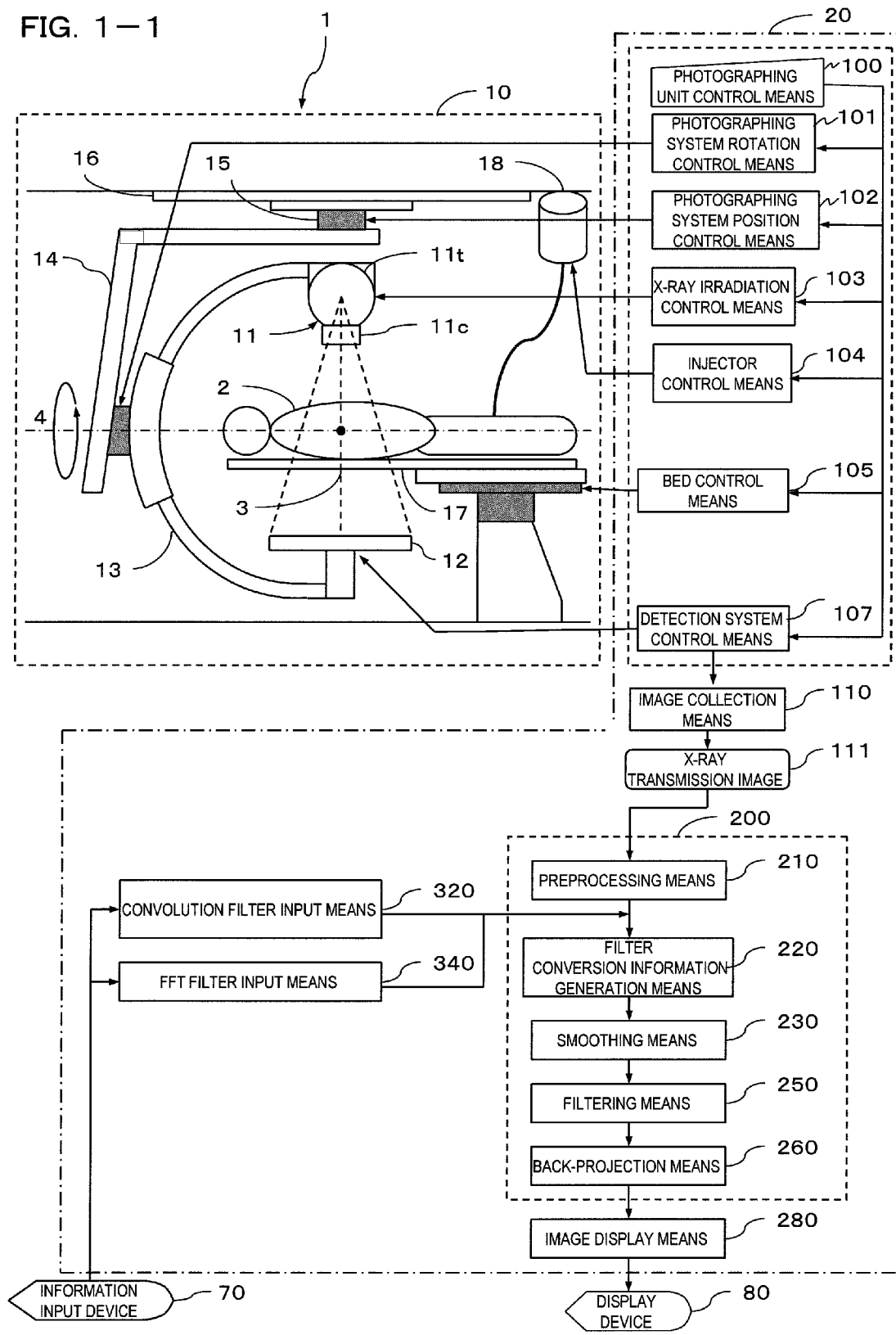
FIG. 1-1 is a schematic configuration diagram showing a cone-beam X-ray CT apparatus (C-arm type) 1 to which the present invention is applied.

Hereinafter, embodiments of an X-ray CT apparatus related to the present invention will be described in detail using the accompanying drawings. In all drawings for explaining the embodiments of the present invention, the same reference numerals are given to elements with the same functions, and repeated explanation thereof will be omitted.

<Schematic Configuration>

Figures 1, 2:
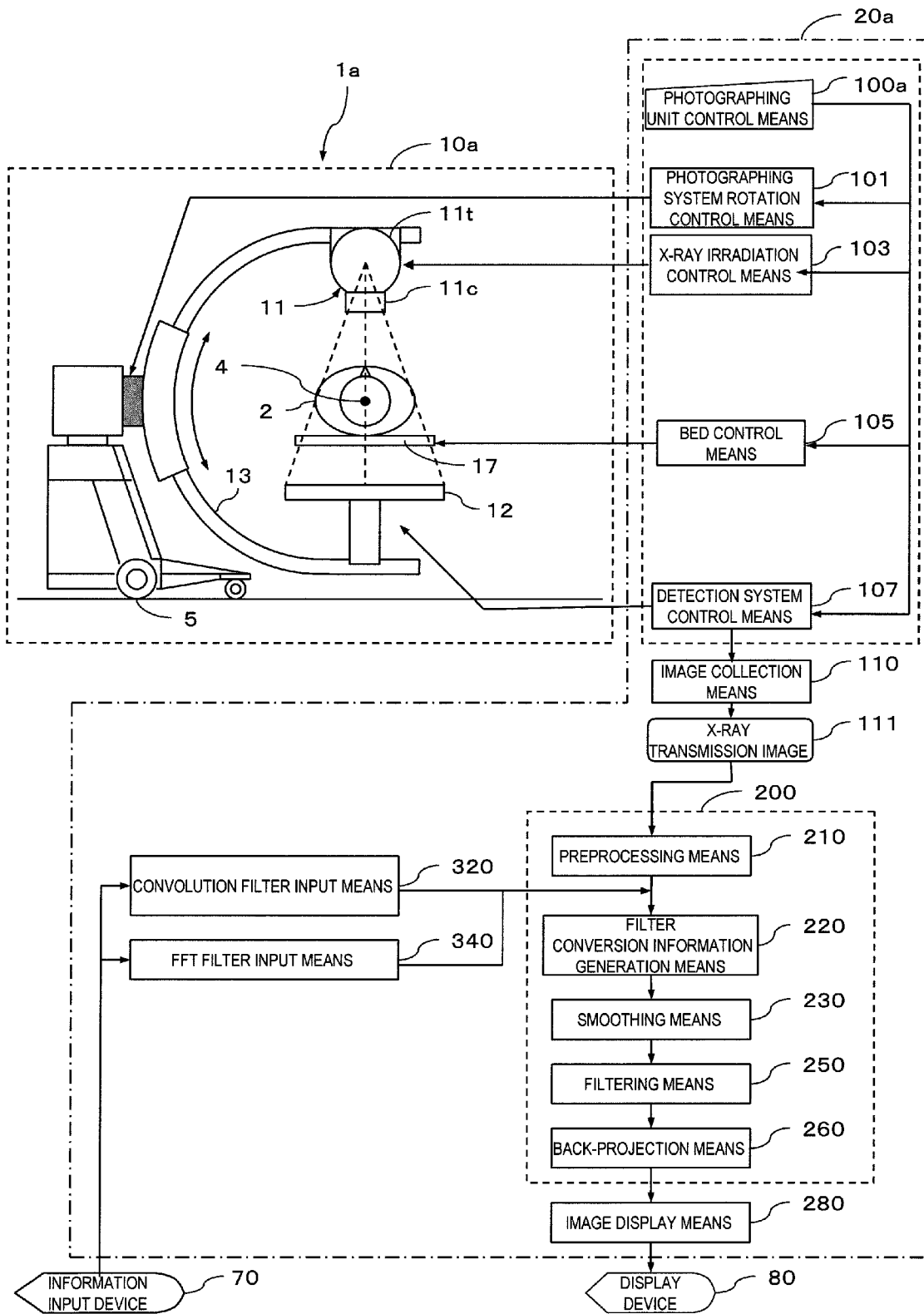
Figure 2:
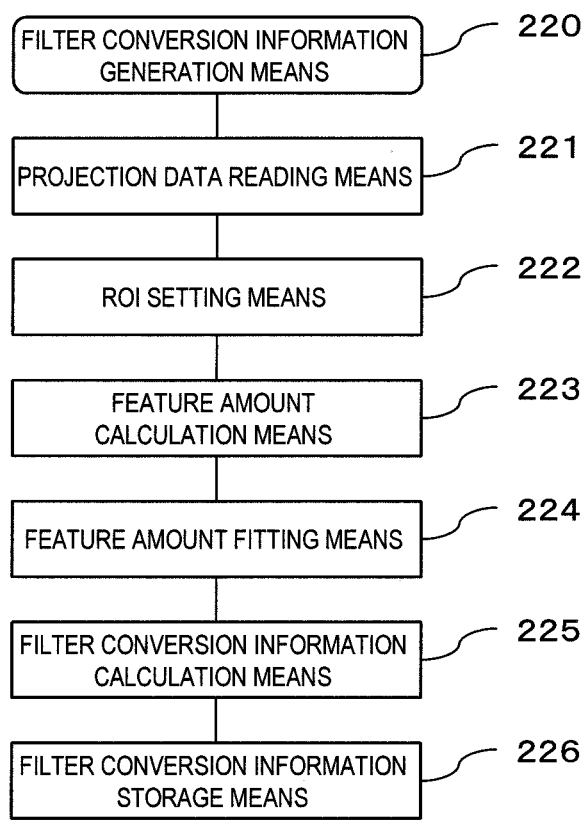

First, the schematic configuration of a cone-beam X-ray CT apparatus to which the present invention is applied will be described on the basis of FIGS. 1-1 and 1-2. FIG. 1-1 is a schematic configuration diagram showing a cone-beam X-ray CT apparatus (C-arm type) 1 to which the present invention is applied. FIG. 1-2 is a schematic configuration diagram showing a C-arm type cone-beam X-ray CT apparatus 1a mounted in a movable X-ray apparatus to which the present invention is applied.

The cone-beam X-ray CT apparatus 1 shown in FIG. 1-1 includes an imaging unit 10 that irradiates an object 2 with X-rays and captures an X-ray transmission image 111 of the object 2 and a control operation unit 20 that controls each component of the imaging unit 10 or reconstructs a three-dimensional CT image of the object 2 on the basis of the X-ray transmission image 111. In addition, the cone-beam X-ray CT apparatus 1 includes a display device 80 that displays an image and an information input device 70 for inputting the parameters or the position of an image displayed on the display device 80, such as a mouse, a keyboard, or a track ball.

The C-arm type cone-beam X-ray CT apparatus 1a mounted in the movable X-ray apparatus shown in FIG. 1-2 includes an imaging unit 10a and a control operation unit 20a that controls each component of the imaging unit 10a or reconstructs a three-dimensional CT image. A wheel 5 is mounted in the cone-beam X-ray CT apparatus 1a, so that the cone-beam X-ray CT apparatus 1a can move between an examination room and an operating room.

Incidentally, there is a central axis of rotation 4 in a direction parallel to the plane of the drawing in FIG. 1-1 so that an X-ray source 11 and a two-dimensional X-ray detector 12 rotate around the central axis of rotation 4, while there is a central axis of rotation 4 in a direction perpendicular to the plane of the drawing in FIG. 1-2 so that the X-ray source 11 and the two-dimensional X-ray detector 12 slide and rotate within a plane parallel to the plane of the drawing. However, even if the cone-beam X-ray CT apparatus 1 in FIG. 1-1 slide-rotates within the plane parallel to the plane of the drawing, the cone-beam X-ray CT apparatus 1a mounted in the movable X-ray apparatus in FIG. 1-2 may rotate.

Hereinafter, each component shown in FIG. 1-1 will be described mainly, and components shown in FIG. 1-2 will be described as necessary.

(Imaging Unit 10)

The imaging unit 10 includes a bed 17, the X-ray source 11 that irradiates the object 2 lying on the bed 17 with X-rays, the two-dimensional X-ray detector 12 that is disposed opposite the X-ray source 11 and outputs an X-ray transmission image 111 by detecting X-rays transmitted through the object 2, a C-type arm 13 that mechanically connects the X-ray source 11 and the two-dimensional X-ray detector 12 to each other, a C-type arm holder 14 that holds the C-type arm 13, and a ceiling support 15 that fixes the C-type arm holder 14 to the ceiling, a ceiling rail 16 that supports the ceiling support 15 so as to be movable in a two-dimensional direction of front and rear and left and right in the state shown in the drawing, and an injector 18 that injects a contrast medium into the object 2.

The X-ray source 11 includes an X-ray tube 11$t$ that generates X-rays and a collimator 11$c$ that controls the direction of X-ray irradiation from the X-ray tube 11$t$ in a conical, quadrangular pyramid, or multi-side pyramid shape.

As the two-dimensional X-ray detector 12, for example, a flat panel detector (hereinafter, referred to as an "FPD") that uses a TFT element is used. In addition, as another example of the two-dimensional X-ray detector 12, it is also possible to use a two-dimensional X-ray detector formed by a combination of an X-ray image intensifier that converts an X-ray transmission image into a visible light image, an optical lens that forms an image of the X-ray image intensifier, and a CCD television camera that captures a visible image of the X-ray image intensifier formed by the optical lens. In addition, the imaging field of view of the two-dimensional X-ray detector 12 may be any shape, such as a circular shape or a rectangular shape.

The above-described C-type arm 13 performs rotational movement around the central axis of rotation 4 at predetermined projection angles when imaging the object 2. Accordingly, the X-ray source 11 and the two-dimensional X-ray detector 12 perform rotational movement on a circular orbit on almost the same plane while maintaining the opposite arrangement, thereby performing X-ray imaging. For this rotational movement, there are geometric parameters for imaging that are used for image reconstruction operation. An orbital plane of rotation (midplane) 3, which is a plane including a circular orbit that the X-ray source 11 traces when the C-type arm 13 performs rotational movement, and the central axis of rotation 4 are included in the geometric parameters for imaging.

(Control Operation Unit 20)

The control operation unit 20 includes imaging unit control means 100 for controlling the imaging unit 10, image collection means 110 for collecting and storing the X-ray transmission image 111 output from the imaging unit 10, reconstruction means 200 for reconstructing a three-dimensional CT image on the basis of the collected X-ray transmission image 111, image display means 280 for displaying the three-dimensional CT image generated by the reconstruction means 200, convolution filter input means 320 for inputting the generation conditions used when the reconstruction means 200 generates a convolution filter, and FFT filter input means 340 for inputting the generation conditions used when the reconstruction means 200 generates a Fourier transform (hereinafter, a Fast Fourier Transform is simply described as an FFT) filter. In addition, the convolution filter is a coefficient superimposed to a corresponding pixel value and the surrounding pixel value when performing image processing, such as smoothing or sharpening, using convolution operation on image space. In addition, the FFT filter is a coefficient for performing an FFT transform of two-dimensional image space for each line (in a one-dimensional manner) and being superimposed for each frequency in the line data generated by the FFT transform. In addition, details of the generation conditions used to generate the convolution filter and the generation conditions used to generate the FFT filter will be described later using FIGS. 5 and 6 and the like.

(Imaging Unit Control Means 100)

The imaging unit control means 100 includes imaging system rotation control means 101 for controlling the rotational movement of the C-type arm 13 around the central axis of rotation 4, imaging system position control means 102 for controlling the position of the C-type arm 13 with respect to the object 2 in a two-dimensional manner by controlling the position of the ceiling support 15 on the ceiling rail 16, X-ray irradiation control means 103 for controlling the ON and OFF states and the like of tube current flowing through the X-ray tube 11t, injector control means 104 for controlling the injection amount and injection timing of a contrast medium injected into the object 2 by the injector 18, bed control means 105 for controlling the position of the bed 17 to adjust the position of the object 2, and detection system control means 107 for controlling the imaging of the X-ray transmission image 111 by the two-dimensional X-ray detector 12. In addition, for the rotation direction of the C-type arm 13, as described above, the central axis of rotation 4 may be located in a direction parallel to the plane of the drawing so that the X-ray source 11 and the two-dimensional X-ray detector 12 rotate around the central axis of rotation 4 (FIG. 1-1), the central axis of rotation 4 may be located in a direction perpendicular to the plane of the drawing so that the X-ray source 11 and the two-dimensional X-ray detector 12 slide-rotate within a plane parallel to the plane of the drawing (FIG. 1-2), or both operation rotations may be made.

(Reconstruction Means 200)

The reconstruction means 200 includes preprocessing means 210, filter conversion information generation means 220, smoothing means 230, filtering means 250, and back-projection means 260.

The preprocessing means 210 converts the X-ray transmission image 111 collected by the image collection means 110 into an X-ray absorption coefficient distribution image (hereinafter, referred to as "projection data 211"). In the present embodiment, first, a natural logarithm conversion operation is performed on each item of pixel data of an X-ray transmission image of the air imaged in advance in a state where the object 2 and the bed 17 are not disposed in the imaging field of view. Then, a natural logarithm conversion operation is performed on each item of pixel data of an X-ray transmission image imaged in a state where the object 2 is placed on the bed 17. In addition, the projection data 211 is obtained by subtracting the X-ray transmission image of the object 2 (and the bed 17), on which the natural logarithm conversion operation has been performed, from the X-ray transmission image of the air on which the above-described natural logarithm conversion operation has been performed.

Next, components of the filter conversion information generation means 220 included in the cone-beam X-ray CT apparatus (C-arm type) 1 in FIG. 1-1 and the C-arm type cone-beam X-ray CT apparatus 1a in FIG. 1-2 will be described on the basis of FIG. 2. FIG. 2 is a block diagram showing components of the filter conversion information generation means 220 in the present invention.

The filter conversion information generation means 220 is means for characterizing the present invention, and generates filter conversion parameters for generating an FFT filter on frequency space and a convolution filter as an image processing filter, which are used by the smoothing means 230 and the filtering means 250. The filter conversion information generation means 220 includes projection data reading means 221, ROI setting means 222, feature amount calculation means 223, feature amount fitting means 224, filter conversion information calculation means 225, and filter conversion information storage means 226. These components are formed by software that realizes the function of each component and hardware that executes this software, such as an operation and control device, an input/output device, and a storage device. The function of each component is realized by cooperation of the above-described software and hardware.

The projection data reading means 221 reads the projection data 211 generated by the preprocessing means 210. The ROI setting means 222 sets a calculation region of the projection data 211. The feature amount calculation means 223 calculates feature amounts (an average value, a standard deviation, and the like) of the pixel value near each point of the projection data 211 in the calculation region set by the ROI setting means 222. The feature amount fitting means 224 fits the feature amounts of each point of the projection data 211, which is calculated by the feature amount calculation means 223, as a function of the coordinate value of projection data. The filter conversion information calculation means 225 converts the fitting result of the feature amount fitting means 224 into a parameter of a convolution filter. The filter conversion information storage means 226 stores the filter conversion parameter as a function of the coordinate value of projection data. In addition, the above calculation of the feature amounts does not need to be performed for all points on the image of the projection data 211, and it is sufficient to set a calculation region for points that are appropriately thinned out in all directions and to calculate the feature amounts. By the feature amount fitting means 224 and the filter conversion information calculation means 225, it is possible to calculate filter conversion parameters of all points of the projection data 211.

Figure 3:
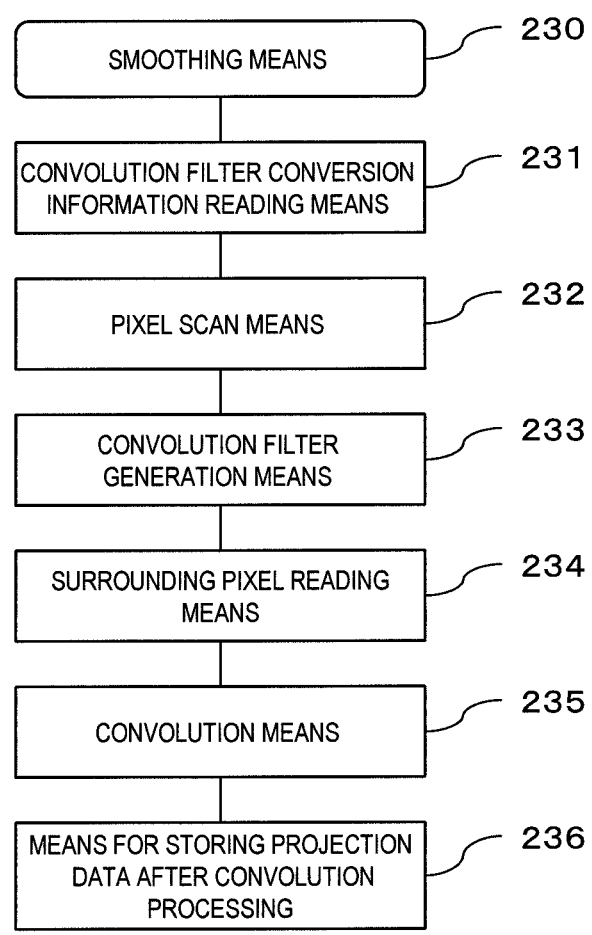
FIG. 3 is a block diagram showing components of smoothing means 230.

Next, components of the smoothing means 230 included in the cone-beam X-ray CT apparatus (C-arm type) 1 in FIG. 1-1 and the C-arm type cone-beam X-ray CT apparatus 1a in FIG. 1-2 will be described on the basis of FIG. 3. FIG. 3 is a block diagram showing components of the smoothing means 230.

The smoothing means 230 generates a convolution filter for each point of the projection data 211 using the generation conditions of the convolution filter input by the convolution filter input means 320 and the filter conversion parameters, which are generated by the filter conversion information generation means 220 and stored in the filter conversion information storage means 226, performs a two-dimensional convolution operation on the projection data 211. As shown in FIG. 3, the smoothing means 230 includes convolution filter conversion information reading means 231, pixel scan means 232, convolution filter generation means 233, surrounding pixel reading means 234, convolution means 235, and means for storing projection data after convolution processing 236. These components are formed by software that realizes the function of each component and hardware that executes this software, such as an operation and control device, an input/output device, and a storage device. The function of each component is realized by cooperation of the above-described software and hardware.

The convolution filter conversion information reading means 231 reads the filter conversion parameters generated by the filter conversion information generation means 220. The pixel scan means 232 scans the coordinate value (coordinates and the pixel value of the coordinates) of the projection data 211, and the convolution filter generation means 233 generates a convolution filter corresponding to each point of the projection data from the convolution filter generation conditions and the filter conversion parameters. The pixel scan means 232 scans the projection data 211 to read the coordinate value (coordinates and the pixel value of the coordinates) of each point of the projection data.

The surrounding pixel reading means 234 reads the value (pixel value) of projection data of a point (hereinafter, referred to as a "surrounding pixel") near a point (hereinafter, referred to as a "projection pixel"), for which a convolution filter is to be generated, on the basis of the coordinate value scanned by the pixel scan means 232. The convolution means 235 performs a convolution operation on the projection pixel by applying the convolution filter generated by the convolution filter generation means 233 to the value (pixel value) of the projection pixel and the value of the projection pixel and the values of surrounding pixels read by the surrounding pixel reading means 234. The means for storing projection data after convolution processing 236 stores a convolution operation result.

Figure 4:
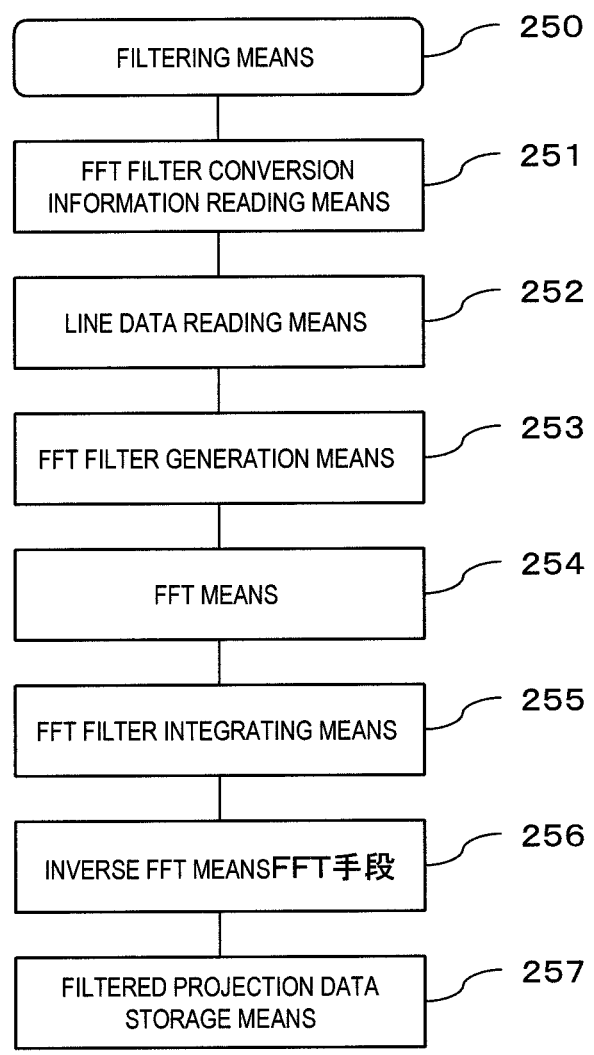
FIG. 4 is a block diagram showing components of filtering means 250.
Figure 15:
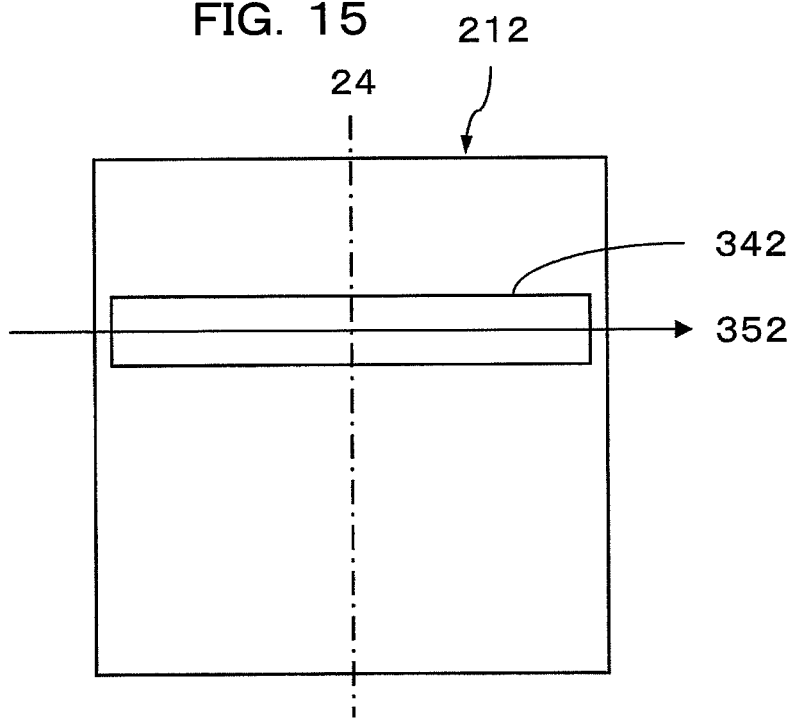
FIG. 15 is an explanatory view showing the filtering process.

Next, components of the filtering means 250 included in the cone-beam X-ray CT apparatus (C-arm type) 1 in FIG. 1-1 and the C-arm type cone-beam X-ray CT apparatus 1a in FIG. 1-2 will be described on the basis of FIGS. 4 and 15. FIG. 4 is a block diagram showing components of the filtering means 250. FIG. 15 is an explanatory view showing a filtering process.

The filtering means 250 performs an FFT filtering process by generating an FFT filter corresponding to each horizontal line of projection data (hereinafter, referred to as "projection data after convolution processing") 212, on which a convolution operation has been performed, using the generation conditions of the FFT filter input by the FFT filter input means 340 and the filter conversion parameters generated by the filter conversion information generation means 220. As shown in FIG. 4, the filtering means 250 includes FFT filter conversion information reading means 251, line data reading means 252, FFT filter generation means 253, FFT means 254, FFT filter integrating means 255, inverse FFT means 256, and filtered projection data storage means 257. These components are formed by software that realizes the function of each component and hardware that executes this software, such as an operation and control device, an input/output device, and a storage device. The function of each component is realized by cooperation of the above-described software and hardware.

The FFT filter conversion information reading means 251 reads the filter conversion parameters generated by the filter conversion information generation means 220 and stored in the filter conversion information storage means 226. The line data reading means 252 reads horizontal line data subjected to filtering process at a time, for example, horizontal line data 352 in FIG. 15, from the projection data 212. The FFT filter generation means 253 generates an FFT filter for each line from the FFT filter generation conditions and the filter conversion parameters. The FFT means 254 converts the horizontal line data 352 into frequency data, and the FFT filter integrating means 255 integrates the FFT filter generated by the FFT filter generation means 253 in the frequency data. The inverse FFT means 256 restores the frequency data to real space data, and the filtering result is stored in the filtered projection data storage means 257.

The back-projection means 260 performs a back-projection operation on the projection data after filtering to generate a three-dimensional CT image of the object 2.

(Convolution Filter Input Means 320)

Figure 5:
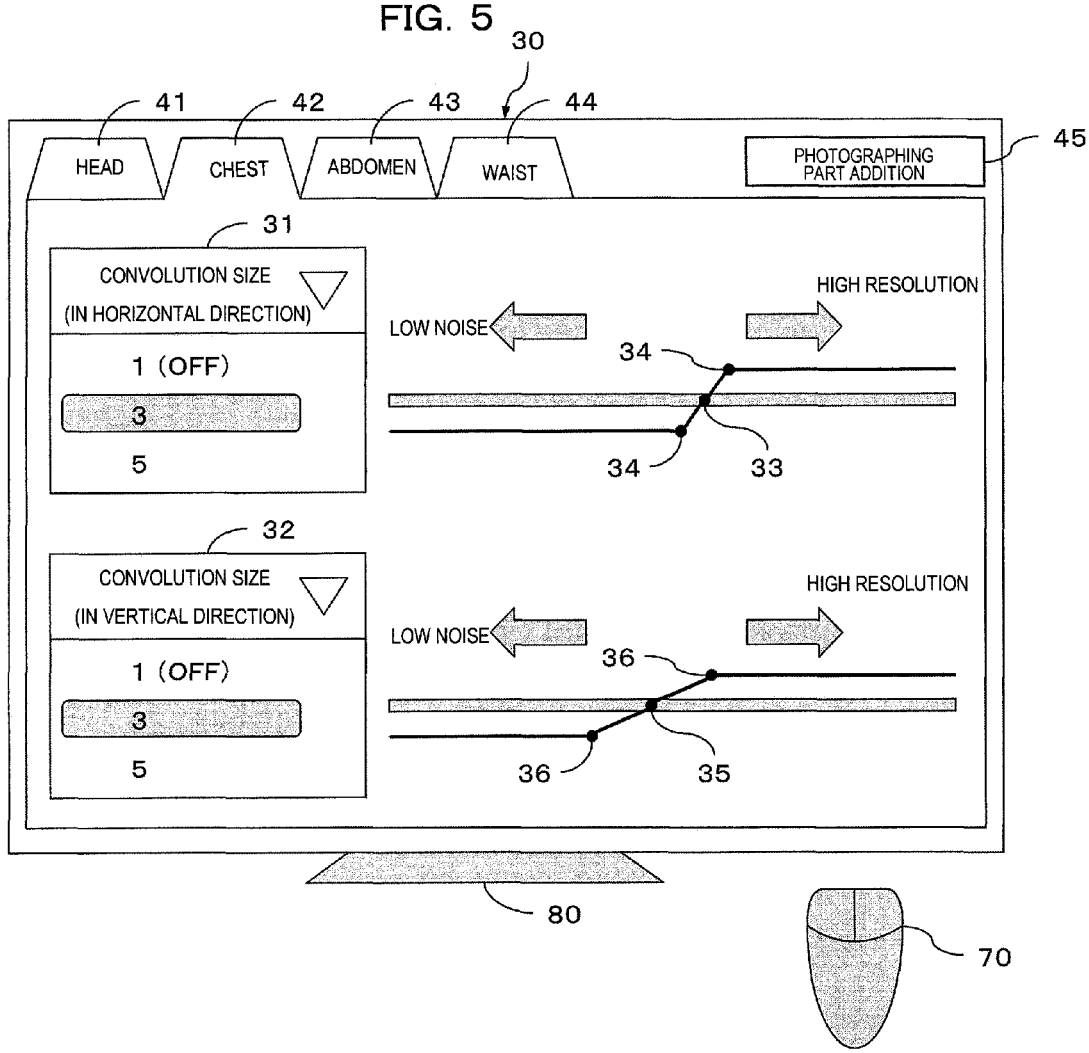
FIG. 5 is a schematic diagram showing an example of a convolution filter setting screen 30.

The convolution filter input means 320 sets the generation conditions of the two-dimensional convolution filter generated by the convolution filter generation means 233. Hereinafter, an example of the GUI that the convolution filter input means 320 uses will be described on the basis of FIG. 5. FIG. 5 is a schematic diagram showing an example of a convolution filter setting screen 30.

Tabs 41 to 44 in FIG. 5 are imaging part selection tabs, and the convolution filter generation conditions for various imaging parts, such as head, chest, abdomen, and waist, can be separately set. FIG. 5 shows a case where the chest condition setting tab 42 is selected. A button 45 is an imaging part addition button, and the conditions of other imaging parts, such as neck and limbs, can be added. A list box 31 is a list box for selecting the size of the convolution filter in a horizontal direction, and the value of "1", "3", or "5" can be selected.

A list box 32 is a list box for selecting the size of the convolution filter in a vertical direction, and the value of "1", "3", or "5" can be selected. Here, when the size of the convolution filter "1" is selected in the list boxes 31 and 32, it means that a convolution operation in the horizontal or vertical direction is not performed (OFF setting).

Points 33 and 35 of FIG. 5 are convolution filter function threshold value setting points in the horizontal or vertical direction. By dragging the points 33 and 35 to the left or right, it is possible to change a horizontal filter function threshold value μa or a vertical filter function threshold value μb. The "filter function threshold value" referred to herein is a value that defines how much the smoothing process is performed (how much the sharpening process is not performed). When a user wants an image with relatively low noise, it is necessary to execute the smoothing process relatively strongly (in other words, it is necessary to execute the sharpening process relatively weakly). In this case, the filter function threshold value is set to a relatively small value. On the other hand, when a user wants an image with relatively high resolution, it is necessary to execute the smoothing process relatively weakly (in other words, it is necessary to execute the sharpening process relatively strongly). In this case, the filter function threshold value is set to a relatively large value.

In addition, points 34 and 36 are convolution filter function variation setting points in the horizontal or vertical direction. By changing the slope of the filter function threshold value boundary, it is possible to change a horizontal filter function variation βa or a vertical filter function variation βb. The "filter function variation" referred to herein is a value that defines a variation of the filter function applied when the smoothing process is performed relatively strongly and a variation of the filter function used when the smoothing process is performed relatively weakly. The relationship between the size of the filter function threshold value and the size of the smoothing process and the relationship between the size of the filter function variation and the size of the smoothing process will be further described in the following "parameters of Fermi distribution function". Details of the process when the convolution filter generation means 233 generates a convolution filter using the filter function threshold values μa and μb and the filter function variations βa and βb will be described later.

(FFT Filter Input Means 340)

Figure 6:
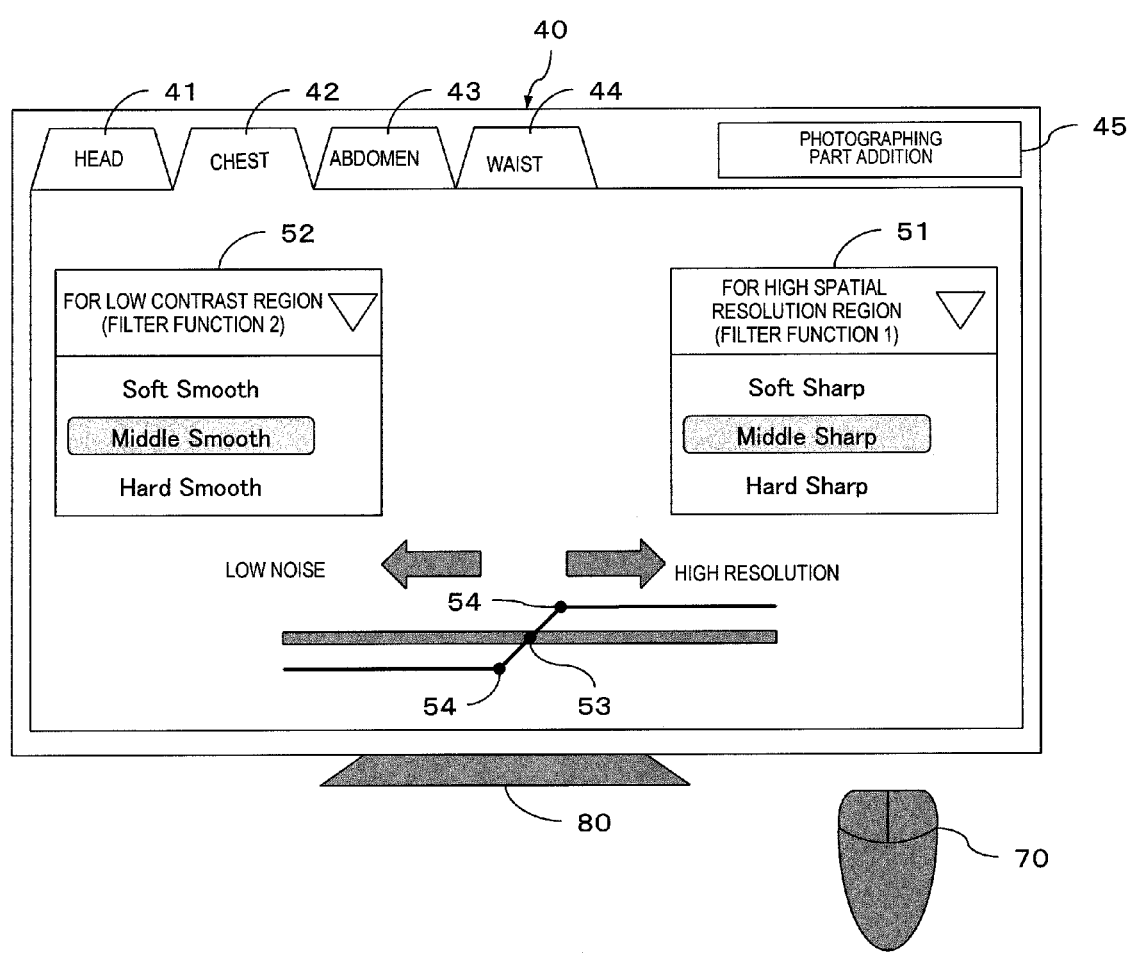
FIG. 6 is a schematic diagram showing an example of an input filter setting screen 40.

The FFT filter input means 340 sets the generation conditions of the FFT filter generated by the FFT filter generation means 253. Hereinafter, an example of the GUI that the FFT filter input means 340 uses will be described on the basis of FIG. 6. FIG. 6 is a schematic diagram showing an example of an FFT filter setting screen 40. Similar to FIG. 5, tabs 41 to 44 are imaging part selection tabs, and a button 45 is an imaging part addition button. FIG. 6 shows a case where the chest condition setting tab 42 is selected.

A list box 51 is a list box for selecting a filter function for a high spatial resolution region, and a list box 52 is a list box for selecting a filter function for a low contrast region. Using these list boxes, the generation conditions that the FFT filter generation means 253 uses are selected. A point 53 is an FFT filter function threshold value setting point, and a point 54 is an FFT filter function variation setting point. By dragging the points 53 and 54 to the left or right to change the FFT filter function threshold value $\mu_F$ or the slope of the threshold value boundary, it is possible to change the FFT filter function variation $\beta_F$. The "FFT filter function threshold value $\mu_F$" referred to herein is a value that defines the size of the smoothing process using an FFT filter. In addition, the "FFT filter function variation $\beta_F$" is a value that defines the rate of changes of two filter functions (filter functions 1 and 2 in FIG. 6) used in the FFT filtering process. Details of the process when the FFT filter generation means 253 generates an FFT filter using the filter function threshold value $\mu_F$, the filter function variation $\beta_F$, and the selected filter function for a high spatial resolution region and filter function for a low contrast region will be described later.

An example of the specification of the cone-beam X-ray CT apparatuses 1 and 1*a* is as follows. The distance between the X-ray source 11 and the central axis of rotation 4 is 800 mm, and the distance between the central axis of rotation 4 and an X-ray incidence surface of the two-dimensional X-ray detector 12 (FPD) is 400 mm. The X-ray incidence surface has a rectangular shape with a size of 400 mm×300 mm, the number of TFT elements is 2048×1536, and a gap between elements is 0.2 mm. When X-rays are incident on the FPD, the X-rays are first converted into light by a luminous body, such as CsI, on the X-ray incidence surface, and the light signal is converted into electric charges by a photodiode. The accumulated electric charges are converted into digital signals at the fixed frame rate by TFT elements and are read. In the rotational imaging mode, binning of "2×2" TFT elements is performed, and the X-ray transmission image 111 is read under the conditions of the image size of 1024×768, the pixel pitch of 0.4 mm, and 30 frames per second. The imaging system rotation control means 101 moves the two-dimensional X-ray detector 12 from the direction (−100°) of the left hand of the object 2 to the direction (+100°) of the right hand of the object 2 through the ceiling direction (0°). As a result, the X-ray transmission image 111 of the object 2 is imaged over a projection angle of 200°. For example, the rotation speed of the C-type arm 13 is 40° per second, and the scan time is 5 seconds.

<Outline of Operation>

Next, the outline of operation in imaging by the cone-beam X-ray CT apparatus 1 will be described.

In the cone-beam X-ray CT apparatus 1, first, the imaging system rotation control means 101 starts the rotation of the C-type arm 13 around the central axis of rotation 4. After the elapse of a period of rotational acceleration, the X-ray irradiation control means 103 emits X-rays from the X-ray tube 11*t*, and the detection system control means 107 starts imaging using the two-dimensional X-ray detector 12. The X-ray emitted from the X-ray tube 11*t* is transmitted through the object 2 and is then received by the two-dimensional X-ray detector 12. The signal of the two-dimensional X-ray detector 12 is A/D converted and is then recorded on the image collection means 110 as the X-ray transmission image 111 which is a digital signal. In the standard scan mode of the two-dimensional X-ray detector FPD, the number of frames per second is 30, and the projection angle distance in rotational imaging is 1.33°. Accordingly, the 150 X-ray transmission images 111 are acquired in 5 seconds. After rotational imaging over 200° is completed, the X-ray irradiation control means 103 ends the X-ray irradiation of the X-ray tube 11*t*, and the imaging system rotation control means 101 stops the rotation after a period of rotational deceleration.

In addition, for example, in an example of the specification when a combination of an X-ray image intensifier, an optical lens, and a CCD television camera is used as the two-dimensional X-ray detector 12, the diameter of the X-ray image intensifier is 300 mm and the standard scan mode of the CCD television camera is 60 frames per second and the number of scanning lines of 512 or 30 frames per second and the number of scanning lines of 1024. The CCD television camera captures a visible light image of the X-ray image intensifier formed by the optical lens. The X-ray transmission image imaged by the CCD television camera is converted into a video signal and is then A/D converted, and the result is collected in the image collection means 110 as a digital image of 512×512 or 1024×1024.

During the above rotational imaging operation or immediately after the end of rotational imaging, the reconstruction means 200 reads the X-ray transmission image 111 from the image collection means 110 and performs reconstruction operation on the basis of this X-ray transmission image 111, thereby generating a three-dimensional CT image of the object 2. The image display means 280 displays the three-dimensional CT image on the display device 80, such as a CRT device or a liquid crystal display device. In addition, the image display means 280 is also used to display the X-ray transmission image 111 recorded on the image collection means 110. The reconstruction means 200 generates a reconstructed image of the object by reconstructing the X-ray transmission image 111 collected by the image collection means 110, and the image display means 280 displays the reconstructed image on the display device 80.

<Reconstruction Process>

Figure 7:
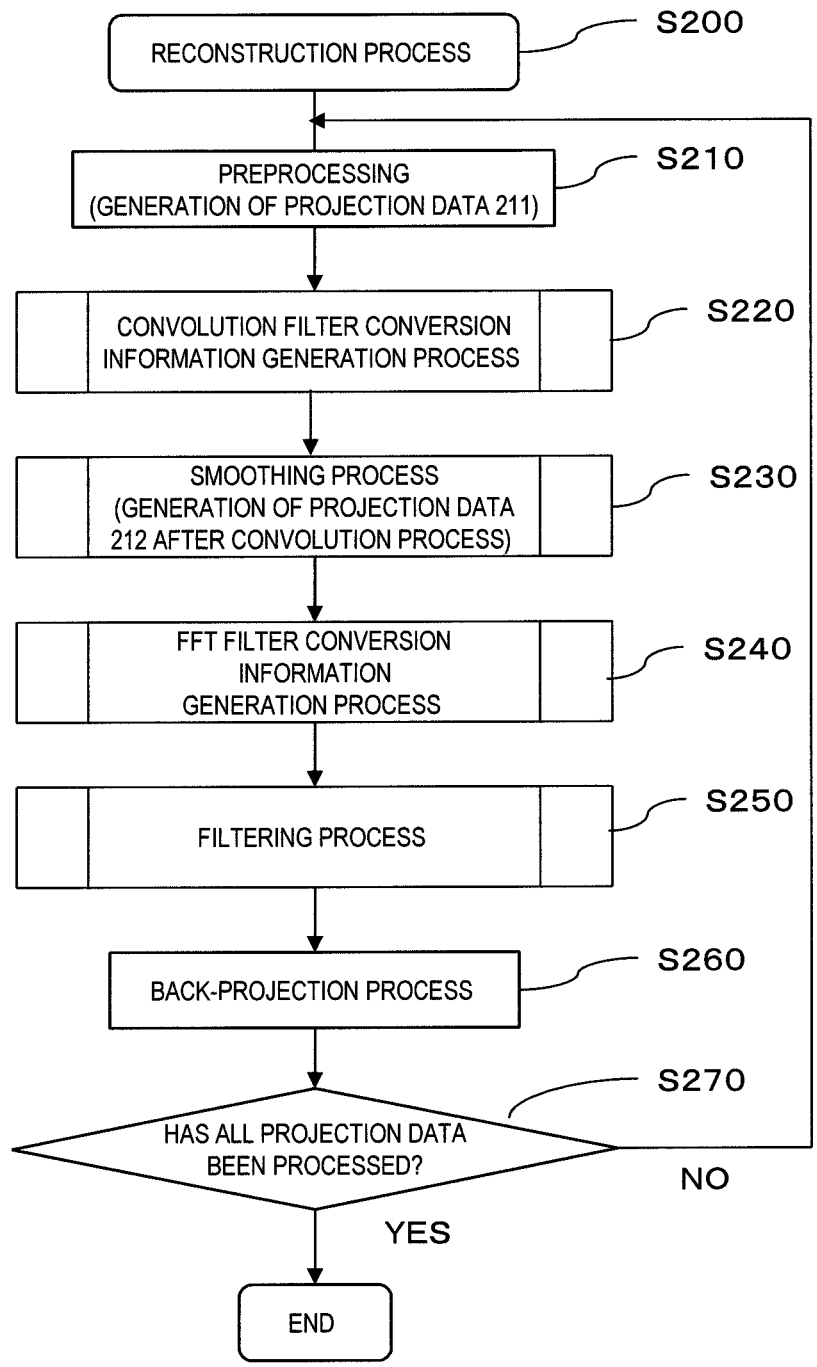
FIG. 7 is a flow chart showing the flow of the reconstruction process (S200) executed by reconstruction means 200.

Next, the flow of a reconstruction process (S200) executed by the reconstruction means 200 will be described on the basis of FIG. 7. FIG. 7 is a flow chart showing the flow of the reconstruction process (S200) executed by the reconstruction means 200. Hereinafter, the reconstruction process (S200) will be described along the order of steps in FIG. 7.

(Step S210)

The preprocessing means 210 performs natural logarithm conversion operation on each X-ray transmission image 111 of the object 2 and the air, which has been collected by the image collection means 110, and converts the result into the projection data 211 (S210).

(Step S220)

The filter conversion information generation means 220 calculates feature amounts (for example, an average value Ac or standard deviation ac of the pixel values of pixels near each point) near each point of the projection data 211, and generates a convolution filter conversion parameter for generating a convolution filter in step S230 (S220).

(Step S230)

The smoothing means 230 generates a convolution filter for each point of the projection data 211 using the convolution filter conversion parameter generated in step S220 and the convolution filter generation conditions set in advance by the user using the convolution filter input means 320, and performs two-dimensional convolution operation for each point (S230).

(Step S240)

The filter conversion information generation means 220 calculates feature amounts (for example, an average value $A_F$ or a standard deviation $\sigma_F$) of the pixel value of each item of the horizontal line data of the projection data 212 on which convolution processing has been performed, and generates an FFT filter conversion parameter for generating an FFT filter in step S250 (S240).

(Step S250)

The filtering means 250 generates an FFT filter, which corresponds to each horizontal line of the projection data 212 on which convolution processing has been performed, using the FFT filter conversion parameter generated in step S240 and the FFT filter generation conditions set in advance by the user using the FFT filter input means 340, and performs an FFT filtering process (S250).

(Step S260)

The back-projection means 260 performs back-projection operation using the projection data after the FFT filtering process in step S250 (S260).

(Step S270)

It is determined whether or not the process of steps S210 to S260 has been executed for all of the projection data. When all projection data has not been processed (NO), the process returns to step S210 to execute the process of steps S210 to S260 for the subsequent projection data. If YES, the reconstruction process (S200) ends, and a three-dimensional CT image of the object 2 is output (S270).

Figure 8:
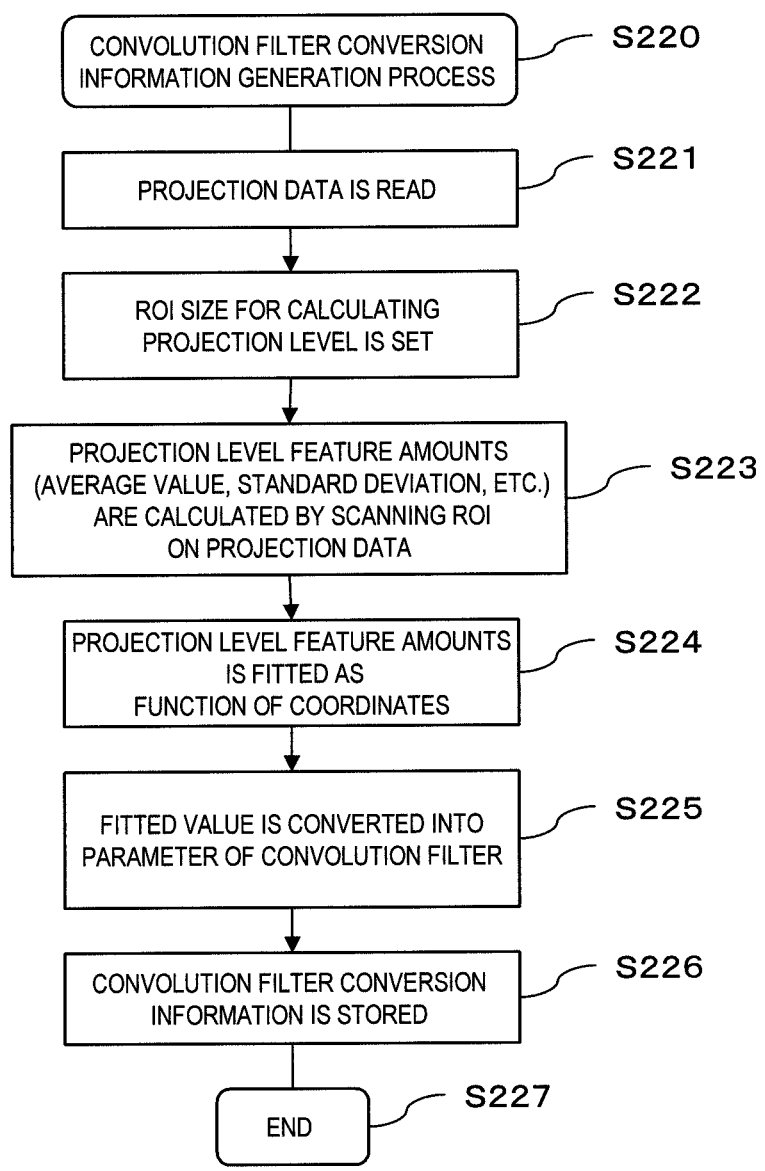
FIG. 8 is a flow chart showing the flow of the convolution filter conversion information generation process (S220).
Figure 9:
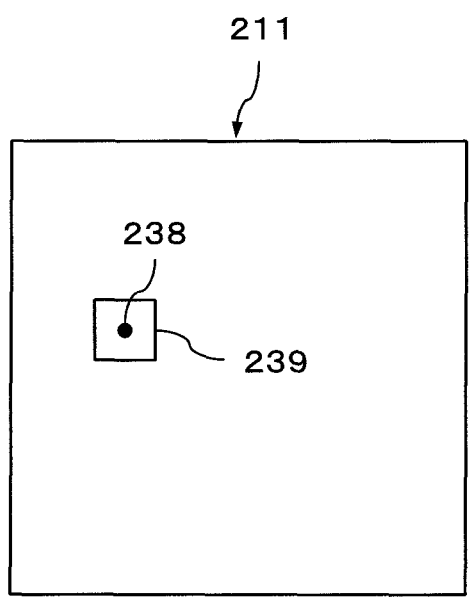
FIG. 9 is an explanatory view showing a feature amount calculation region and the coordinate point on projection data.
Figure 10:
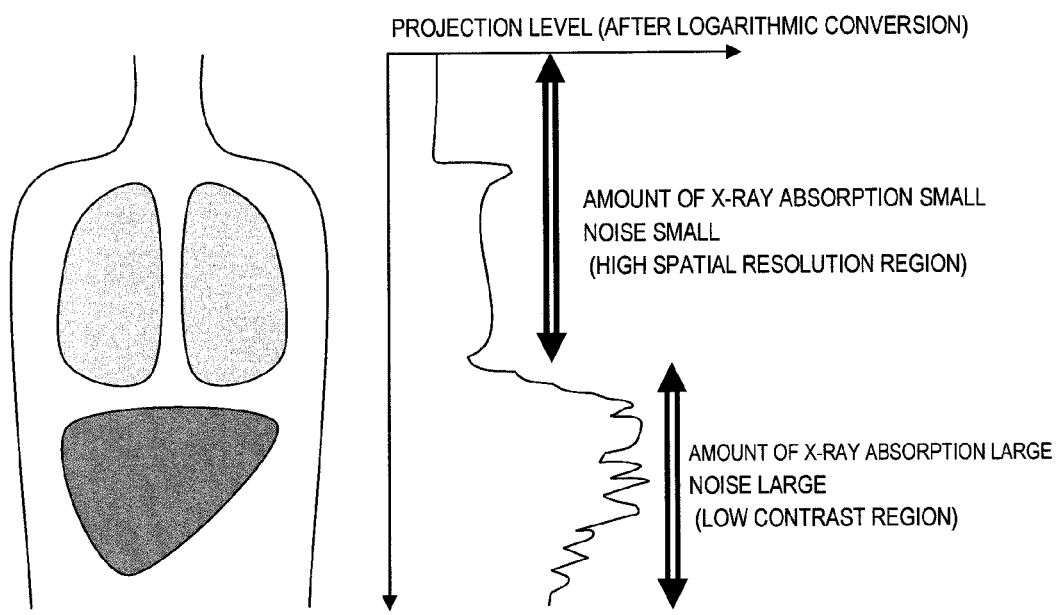
FIG. 10 is a conceptual diagram showing the relationship between the value of projection data and an imaging part.

Hereinafter, details of each process of the above steps S220 to S250, which characterize the present invention, will be described using FIGS. 8, 9, 10, and 12. FIG. 8 is a flow chart showing the flow of the convolution filter conversion information generation process (S220), FIG. 9 is an explanatory view showing a feature amount calculation region and the coordinate point on projection data, FIG. 10 is a conceptual diagram showing the relationship between the value (hereinafter, also referred to as a "projection level") of projection data and an imaging part, and FIG. 12 is an explanatory view showing the curves which show a function of the standard deviation ac of the projection data 211 and a smoothing parameter Wa.

First, the convolution filter conversion information generation process will be described along each step in FIG. 8.

(Step S221)

The projection data reading means 221 reads the projection data 211 generated in step S210 (S221).

(Step S222)

The ROI setting means 222 sets the size of the rectangular or square ROI (calculation region 239) for calculating feature amounts of the projection data 211, as shown in FIG. 9. For example, the ROI size is set to be 15×15 to 25×25 pixels around the coordinate point 238 (S222).

(Step S223)

The feature amount calculation means 223 calculates feature amounts of each point of the projection data 211 by scanning the coordinate point on the projection data 211 and calculating the average value Ac or the standard deviation ac of the pixel values in the ROI region (calculation region 239) designated in step S222. In this case, in order to suppress an influence of the calculated value of standard deviation due to the data deviating largely from the average value, a histogram having a horizontal axis, on which the average value, the maximum value, and the minimum value of pixel values in the ROI are set, is once created for each ROI. In addition, it is also possible to calculate a standard deviation value using only the data existing in the frequency distribution of, for example, ±1/10 from the average value of the pixel values in the ROI (S223). In addition, although the feature amounts have been calculated for each point of the projection data 211 in the present embodiment, it is also possible to calculate feature amounts only for points appropriately thinned out instead of calculating the feature amounts for all points. In this case, as feature amounts of the point of the projection data 211 that has been thinned out, it is possible to use feature amounts of the pixel values acquired from the calculation region including the point.

FIG. 10 shows conceptually a change in the value of projection data in imaging of parts of a chest to abdomen. In the chest region, the amount of X-ray absorption is small. Accordingly, in the projection data after logarithmic conversion, the average value is small and its error (standard deviation) is also small. On the other hand, in the abdomen region, the average value in the projection data after logarithmic conversion is large, and the output value of the X-ray detector is small. Accordingly, it is data with a large error.

The present invention realizes an X-ray CT apparatus capable of generating an X-ray CT image with high spatial resolution by applying a sharpening filter in an imaging part, in which the average value of projection data is small and the standard deviation is small, and of generating an X-ray CT image which has low contrast and is excellent in resolution by applying a smoothing filter to suppress noise in an imaging part, in which an error of projection data is large.

(Step S224)

The feature amount fitting means 224 fits the feature amounts of each point of the projection data 211 calculated in step S223 as a function of the coordinate value of projection data (that is, matches positional information (coordinate value) of each point of the projection data 211 in the horizontal and vertical directions with the feature amounts of the pixel value at the position) (S224). In addition, steps S223 and S224 may be omitted. In this case, for example, a user may input the estimated values of the feature amounts of the pixel value (or the range of feature amounts) on the basis of an imaging part or imaging conditions, and the following filter conversion information may be calculated using the feature amounts of the input pixel value.

(Step S225)

The filter conversion information calculation means 225 converts the fitting result in step S224 into a parameter of a convolution filter, that is, generates a parameter of a convolution filter using the feature amounts of the pixel value included in the fitting result (S225). Details of the parameter of the convolution filter and the process will be described below on the basis of FIG. 12. FIG. 12 is an explanatory view showing the curves which show a function of the standard deviation σc of the projection data 211 and the parameter Wa.

Generally, a convolution filter is standardized so that the sum is set to 1. In addition, parameters that can be changed under the conditions in which the sum of the convolution filter is 1, for example, the parameter Wa in a horizontal direction (u direction in FIGS. 11-1 to 11-3 which will be described) and a parameter Wb in a vertical direction (v direction in FIGS. 11-1 to 11-3 which will be described) can be introduced. Generally, the parameter Wa in the horizontal direction and the parameter Wb in the vertical direction take real values exceeding −0.5 and their maximum values are 1.0.

Convolution operation when the parameter Wa or Wb takes a negative value is an operation of taking a difference from an adjacent pixel. In this case, the convolution operation acts as a sharpening filter. In the following explanation of the present embodiment, it is assumed that the parameters Wa and Wb take positive values (0.0 to 1.0), the convolution operation acts as a smoothing filter, and the sharpening process is performed in the next FFT filtering operation. Therefore, in the following explanation of the smoothing process, the parameter Wa or the parameter Wb is written as the smoothing parameter Wa or the smoothing parameter Wb.

Hereinafter, the function expression in which the filter conversion information calculation means 225 in step S225 sets the parameters Wa and Wb from the feature amounts (the ROI average value Ac and the standard deviation σc) of the projection data 211, which are calculated by the feature amount calculation means 223 in step S223, will be described by way of example. As described above, the smoothing parameters Wa and Wb are assumed to take a value of 0.0 to 1.0. On the other hand, feature amounts (the ROI average value Ac and the standard deviation σc) of the projection data are assumed to take arbitrary real values even though Ac is typically a value of about 0.02/mm (X-ray absorption coefficient of water)×200 mm (body thickness)=4.0 and σc is typically a value of about 0.2. As an example of the function whose input is an arbitrary real value and output is 0 to 1, "Fermi distribution function" f(x) mentioned below is introduced.

[Expression 1]

$$f(x) = \frac{1}{1+e^x}, x = \frac{\mu_a - \sigma_C}{\sqrt{A_C}} \cdot \beta_a \quad (1)$$

In this case, Wa=f(x) can be assumed. Alternatively, a function f(y) is introduced.

[Expression 2]

$$f(y) = \frac{1}{1+e^y}, y = \frac{\mu_b - \sigma_C}{\sqrt{A_C}} \cdot \beta_b \quad (2)$$

In this case, Wb=f(y) can be assumed. In Expressions (1) and (2), μa and μb are filter function threshold values in the horizontal and vertical directions input by the convolution filter input means 320, and βa and βb are filter function variations. From matters described below, a value of about 10 may be the standard value of βa and βb. The "Fermi distribution function" of Expressions (1) and (2) has a characteristic of f(x)+f(−x)=1. 1−Wa=f(−x) or 1−Wb=f(−y) may be used in the operation of calculating a convolution filter illustrated in FIGS. 11-1 to 11-3.

The curve (1) in FIG. 12 (drawn by the solid line in FIG. 12) shows the "Fermi distribution function" f (x). At the time of x=0, that is, standard deviation σc=filter function threshold value μa, f(0)=0.5. f(x) takes a value of about 0.73 at the time of x=−1.0, 0.5 at the time of x=0, and about 0.27 at the time of x=+1.0. For the smoothing parameter Wa determined by the function f(x), when the ROI average value Ac of projection data, the filter function threshold value μa, and the filter function variation βa do not change, x decreases as the standard deviation σc (that is, the amount of noise) of projection data increases, and accordingly, the smoothing parameter Wa increases. That is, generally, in the "Fermi distribution function" f(x), the smoothing parameter Wa=0.5 at the time of filter function threshold value μ=standard deviation σ, Wa>0.5 at the time of μ<σ, and Wa<0.5 at the time of μ>σ. Accordingly, the smoothing process is performed relatively strongly in Wa>0.5, while the smoothing process is performed relatively weakly in Wa<0.5. In addition, if the filter function variation β (β>0) is made to be relatively large under the conditions of μ>σ, x becomes relatively large. Accordingly, since the smoothing parameter W becomes relatively small, a stronger high resolution process is set. In addition, if the filter function variation β (β>0) is made to be relatively large under the conditions of μ<σ, x becomes relatively small. Accordingly, since the smoothing parameter W becomes relatively large, a stronger low-resolution process is set.

The curve (2) in FIG. 12 (drawn by the dotted line in FIG. 12) shows changes in f(x) when the average value Ac and the filter function variation βa are standard values Ac=4.0 and βa=10 and the filter function threshold value μa=±0.2. When the filter function threshold value μa is set to +0.2 at the time of Ac=4.0 and βa=10, x in Expression (1) is increased by 1.0. Accordingly, since the smoothing parameter Wa is decreased for the same standard deviation σC, a high resolution process is set.

On the contrary, when the filter function threshold value μa is set to −0.2, x in Expression (1) is decreased by 1.0. Accordingly, since the smoothing parameter Wa is increased, a low noise process is set. As a result, since low noise setting is made compared with the curve (1) of standard setting, this is equivalent to the curve (3) in FIG. 12 (drawn by the dotted line in FIG. 12).

Although the above is an explanation when calculating the smoothing parameter Wa in the horizontal direction from the filter function threshold value μa, the filter function variation βa, and the ROI average value Ac, and the standard deviation σc, the smoothing parameter Wb in the vertical direction is calculated by Expression in which "a" in the above wording is replaced with "b" and "a" in FIG. 12 is replaced with "b".

In addition, as described previously, it is preferable to suppress the smoothing parameter Wa in the horizontal direction to a small value and to increase the smoothing parameter Wb in the vertical direction from the viewpoint of the spatial resolution of the CT image. In FIG. 5 described earlier, the case is shown in which the filter function threshold value μa in the horizontal direction indicated by the point 33 is set to the relatively large value and the filter function threshold value μb in the vertical direction by the point 35 is set to the relatively small value.

The process in this step is performed for each point of the projection data 211, thereby generating the information in which the coordinate value of each point is matched with the smoothing parameters Wa and Wb.

(Step S226)

The filter conversion information storage means 226 stores the filter conversion information (information in which the convolution filter conversion parameter is a function of the coordinate value of projection data) calculated in step S225 (S226).

Figure 13:
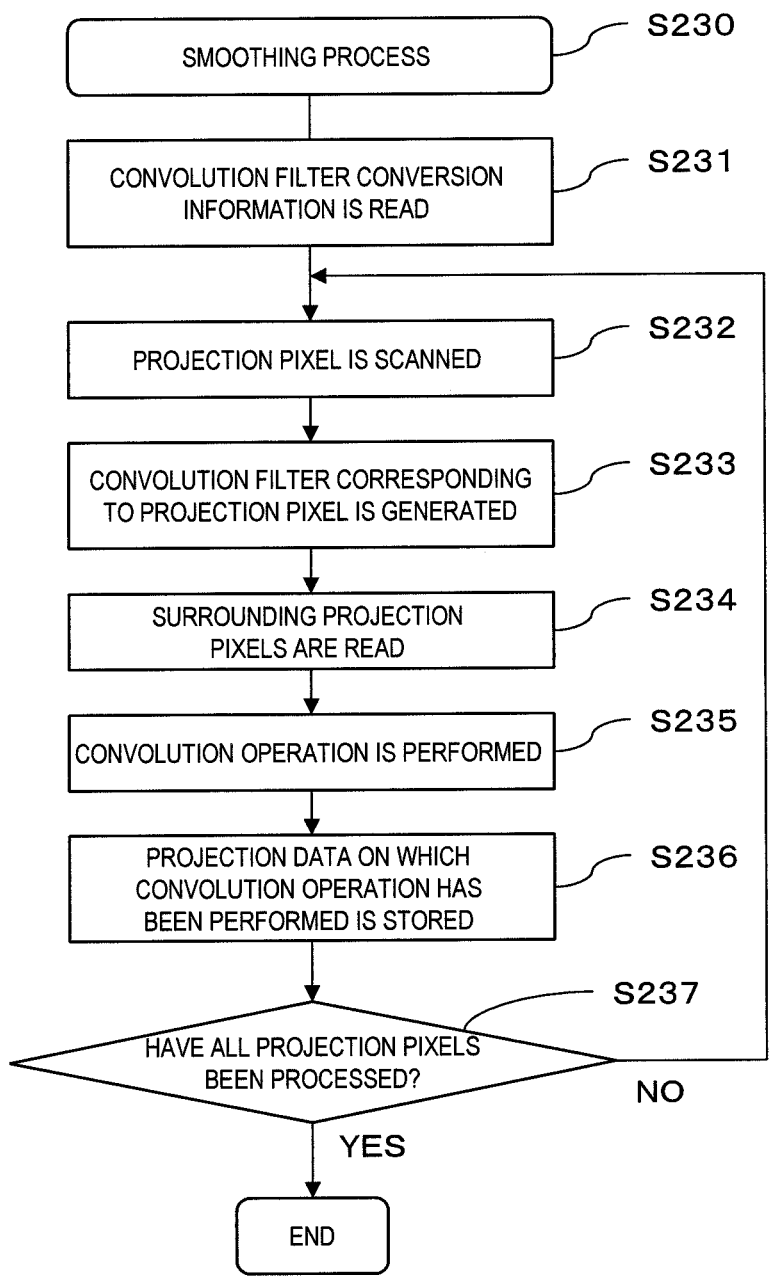
FIG. 13 is a flow chart showing the flow of the smoothing process (S230).

Next, details of the smoothing process (S230) will be described using FIGS. 11-1, 11-2, 11-3, and 13. FIG. 11-1 is an explanatory view illustrating the convolution operation when the size of the convolution filter is 3×3, FIG. 11-2 is an explanatory view illustrating the convolution operation when the size of the convolution filter is 1×3, FIG. 11-3 is an explanatory view illustrating the convolution operation when the size of the convolution filter is 3×5, and FIG. 13 is a flow chart showing the flow of the smoothing process (S230). The following explanation will be given along the order of steps in FIG. 13.

(Step S231)

The convolution filter conversion information reading means 231 reads the convolution filter conversion information generated by the convolution filter conversion information generation process (S220) (specifically, the smoothing parameters Wa and Wb that are stored as a function of the coordinate value of projection data in step S226) (S231).

(Step S232)

The pixel scan means 232 scans the coordinate value (equivalent to the coordinates of a pixel and the pixel value) of each point (hereinafter, referred to as a projection pixel) of the projection data 211 (S232).

(Step S233)

The convolution filter generation means 233 reads the smoothing parameters Wa and Wb corresponding to the coordinate value of each projection pixel using the convolution filter conversion information and generates a convolution filter corresponding to each projection pixel using the smoothing parameters Wa and Wb (S233).

Here, the convolution operation and the process of the convolution filter generation means 233 in the present embodiment will be described by way of example using FIGS. 11-1 to 11-3 and 12. In addition, the convolution operation and the convolution filter generation method are not limited to those described below but may be appropriately changed within a range not departing from the technical concept of the present invention.

FIG. 11-1 is a view schematically showing the convolution operation executed when both the sizes of the convolution filter in the horizontal and vertical directions are set to "3", FIG. 11-2 is a view schematically showing the convolution operation executed when the size of the convolution filter in the horizontal direction is set to "1" (that is, convolution operation in the horizontal direction OFF) and the size of the convolution filter in the vertical direction is set to "3", and FIG. 11-3 is a view schematically showing the convolution operation executed when the size of the convolution filter in the horizontal direction is set to "3" and the size of the convolution filter in the vertical direction is set to "5". In FIG. 11-1, matrices 61, 63, and 65 show the value P(u, v) of a pixel, on which convolution operation is performed, and pixel values of points near the pixel. Matrices 62, 64, and 66 show convolution filters. In addition, a pixel value P' (u, v) after convolution operation corresponding to the pixel value P (u, v) before convolution operation is calculated on the basis of the following Expression (3) for FIG. 11-1 and on the basis of the following Expression (4) for FIG. 11-2.

[Expression 3]

$$P'(u, v) = P(u-1, v-1) \times \frac{Wa \cdot Wb}{(1+2Wa)(1+2Wb)} + \\ P(u, v-1) \times \frac{Wb}{(1+2Wa)(1+2Wb)} + \\ P(u+1, v-1) \times \frac{Wa \cdot Wb}{(1+2Wa)(1+2Wb)} + \\ P(u-1, v) \times \frac{Wa}{(1+2Wa)(1+2Wb)} + \\ P(u, v) \times \frac{1}{(1+2Wa)(1+2Wb)} + \\ P(u+1, v) \times \frac{Wa}{(1+2Wa)(1+2Wb)} + \\ P(u-1, v+1) \times \frac{Wa \cdot Wb}{(1+2Wa)(1+2Wb)} + \\ P(u, v-1) \times \frac{Wb}{(1+2Wa)(1+2Wb)} + \\ P(u+1, v-1) \times \frac{Wa \cdot Wb}{(1+2Wa)(1+2Wb)}$$ (3)

[Expression 4]

$$P'(u, v) = P(u, v-1) \times \frac{Wb}{(1+2Wb)} + \\ P(u, v) \times \frac{1}{(1+2Wb)} + P(u, v+1) \times \frac{Wb}{(1+2Wb)}$$ (4)

In addition, also for FIG. 11-3, the pixel value P'(u, v) after convolution operation is calculated by multiplying the pixel value of the matrix 65 by the weight in the matrix 66 at the same position as the position of the pixel value in the matrix 65, similar to Expression (3) in FIG. 11-1 and Expression (4) in FIG. 11-2.

Convolution filters described in the matrices 62, 64, and 66 are convolution filters using the smoothing parameters Wa and Wb generated by the filter conversion information generation means 220, and are standardized so that the sum is set to 1.

The spatial resolution of a reconstructed CT image largely depends on the resolution of the projection data 211 in the horizontal direction (u direction). Therefore, it is preferable to suppress the smoothing parameter Wa in the horizontal direction (u direction) to 0 or a small value and to increase the smoothing parameter Wb in the vertical direction (v direction). In addition, as illustrated in FIGS. 11-1 to 11-3, it is preferable that the standard size of the convolution filter be set to the size of 1×3 or 3×5 with 3×3 as a standard size. In the present embodiment, since the size of the convolution filter in the horizontal direction is input as 3 and the size of the convolution filter in the vertical direction is input as 3 in the list boxes 31 and 32 of the convolution filter setting screen 30 shown in FIG. 5, a convolution filter with 3×3 size is generated for each point of the projection data 211.

(Step S234)

The surrounding pixel reading means 234 reads pixel values of projection pixels (also referred to as surrounding pixels) located around the projection pixel on which a convolution operation is to be performed (S234). The projection pixels located in the vicinity are used in the following convolution operation.

(Step S235)

The convolution means 235 performs a convolution operation using the convolution filter generated in step S233 and the pixel values of the projection pixel and the surrounding pixels read in steps S232 and S234 (S235). For example, when the filter size of 3×3 is set on the convolution filter setting screen in FIG. 5, the convolution means 235 performs the convolution operation on the basis of Expression (3).

(Step S236)

The means for storing projection data after convolution processing 236 stores the convolution operation result of step S236 (S236).

(Step S237)

It is determined whether or not the process of steps S232 to S236 has been executed for all projection pixels. When all projection pixels have not been processed (NO), the process returns to step S232 to execute the process of steps S232 to S236 for the subsequent projection pixels. If YES, the smoothing process (S230) ends, and the process proceeds to the FFT filter conversion information generation process (S240).

Figure 14:
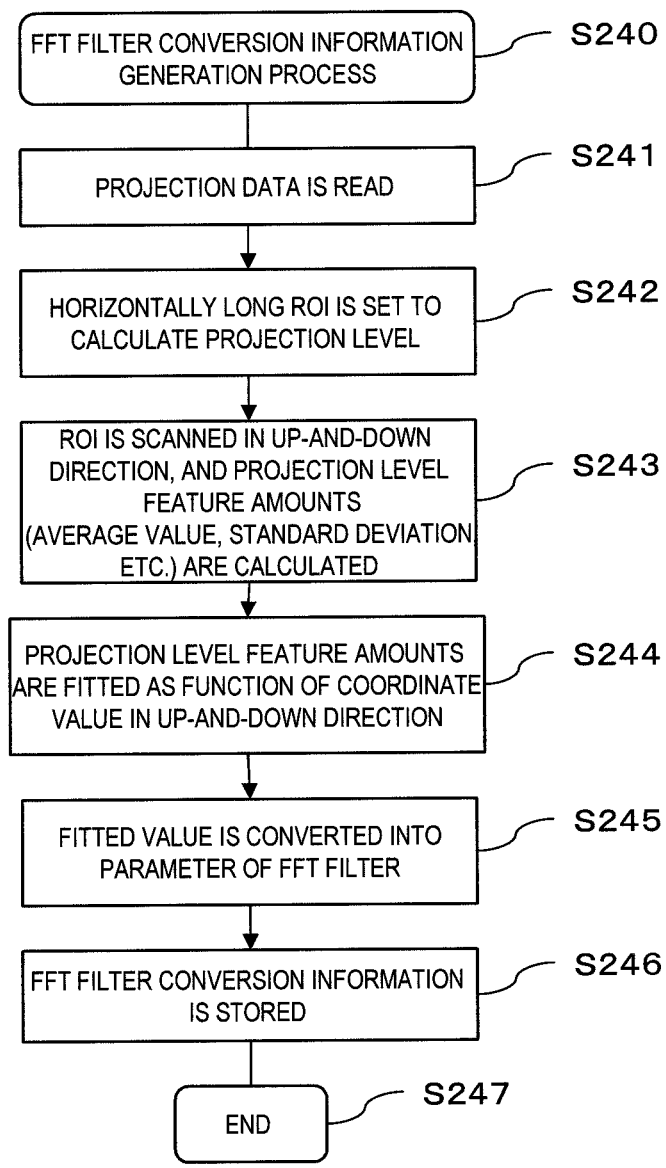
FIG. 14 is a flow chart showing the process flow of the FFT filter conversion information generation process (S240).

Next, details of the FFT filter conversion information generation process (S240) will be described on the basis of FIGS. 14 and 15. FIG. 14 is a flow chart showing the process flow of the FFT filter conversion information generation process (S240), and FIG. 15 is an explanatory view showing the filtering process. In addition, a vertical line 24 in FIG. 15 is a line indicating the projection of the central axis of rotation 4 to the two-dimensional X-ray detector 12, and the filtering process is performed for the horizontal line data 352 along the rotation direction (direction perpendicular to the central axis of rotation 4). Hereinafter, the FFT filter conversion information generation process (S240) will be described along the order of steps in FIG. 14.

(Step S241)

The projection data reading means 221 reads the projection data after convolution processing 212 generated in step S230 (S241).

(Step S242)

The ROI setting means 222 sets the size of a horizontally long rectangular ROI (calculation region 342) shown in FIG. 15 (S242).

(Step S243)

The feature amount calculation means 223 scans the rectangular ROI (calculation region 342) in an up-and-down direction (or called a vertical direction) on the projection data after convolution processing 212, and calculates feature amounts (for example, the average value $A_F$ and standard deviation $\sigma_F$ of the pixel values of pixels in the ROI). In this case, as in the calculation of step S223, in order to suppress an influence of the calculated value of standard deviation due to the data deviating largely from the average value, it is possible to create once a histogram having a horizontal axis, on which the average value, the maximum value, and the minimum value of pixel values in the ROI are set, and to calculate the standard deviation value using only the data existing in the frequency distribution of, for example, ±1/10 from the average value of the pixel values in the ROI (S243).

(Step S244)

The feature amount fitting means 224 fits the feature amounts calculated in step S243 as a function of the coordinate value of projection data in the up-and-down direction (that is, matches positional information of the projection data in the up-and-down direction with the feature amounts at the position) (S244).

(Step S245)

The filter conversion information calculation means 225 converts the fitting result in step S244 into a parameter of an FFT filter. Details of the parameter of the FFT filter and the process will be described below (S245).

Figure 16:
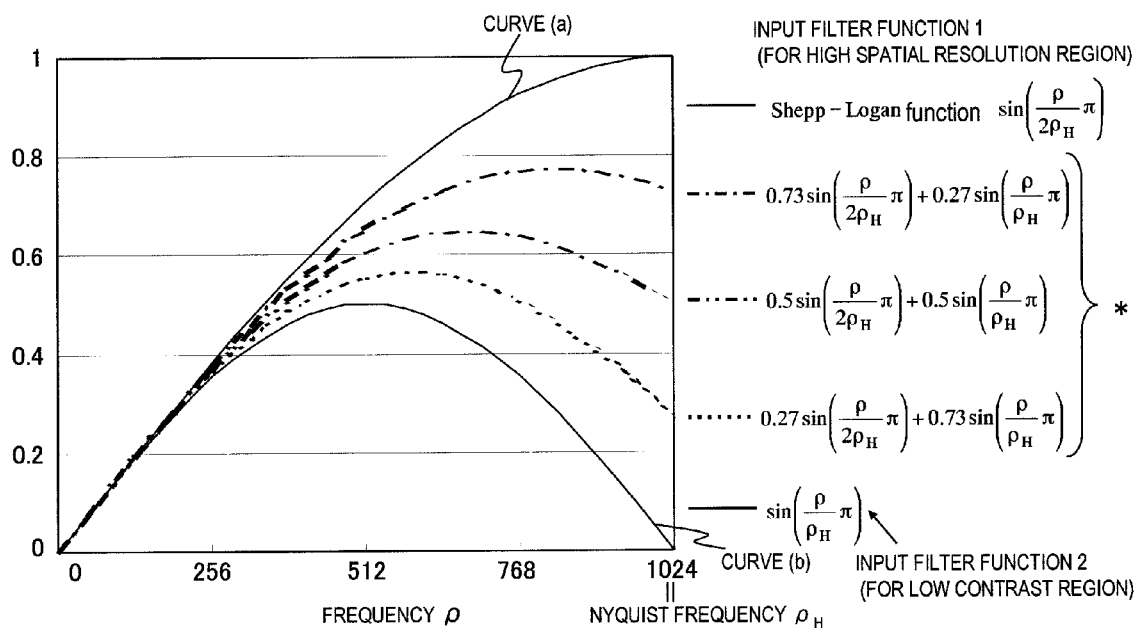
FIG. 16 is an explanatory view showing examples of the FFT filter function input by FFT filter input means 340 and the FFT filter function generated by FFT filter generation means 253.
Figure 17:
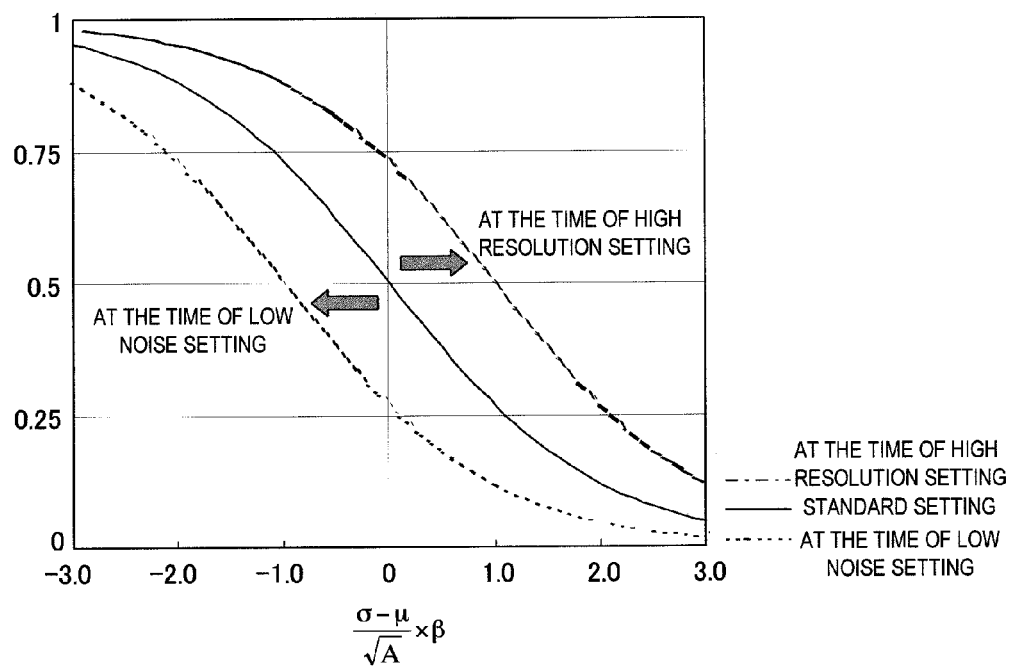
FIG. 17 is an explanatory view showing the curves which show a function of the standard deviation a and the filter function content for a high spatial resolution region.

Here, an FFT filter function and its combination method in the present embodiment will be described by way of example using FIGS. 16 and 17. FIG. 16 is an explanatory view showing examples of the FFT filter function input by the FFT filter input means 340 and the FFT filter function generated by the FFT filter generation means 253, and FIG. 17 is an explanatory view showing the curves which show a function of the standard deviation σ and the filter function content for a high spatial resolution region. In addition, the FFT filter function and its combination method are not limited to those described below but may be appropriately changed within a range not departing from the technical concept of the present invention.

FIG. 16 shows examples of the FFT filter function input by the FFT filter input means 340 and the FFT filter function generated by the FFT filter generation means 253. The uppermost curve (a) and the lowermost curve (b) in FIG. 16 are examples of the FFT filter function for a high spatial resolution region and the FFT filter function for a low contrast region, which are input by the FFT filter input means 340. Three curves (drawn by the dotted lines) in the middle are examples of the FFT filter function that is generated from the linear sum of two input FFT filter functions according to the feature amounts of projection data by the FFT filter generation means 253. The vertical axis is an integrated strength on frequency space executed in the FFT filter integrating means 255, and the horizontal axis indicates a frequency and the unit is [1/Pixel].

The input image of the present embodiment is a 1024×768 image collected by 2×2 binning. Although well known in FFT operation, it is assumed that the FFT filter operation is performed at 2048 points, which are twice 1024 in the horizontal width of the input image, so that so-called aliasing caused by folding does not occur. In this case, the absolute value of the upper limit frequency (called a "Nyquist frequency") is 1024 from the sampling interval, and the frequency takes a value of −1024 to +1024. The FFT filter function is set to take the same value at positive and negative frequencies whose absolute values are equal. FIG. 16 shows an FFT filter function of only the positive frequency. In addition, in the example of FIG. 16, a case is shown in which a Shepp-Logan function is used as the FFT filter function for a high spatial resolution region and a sin function with a ½ period of that of the Shepp-Logan function is used as the FFT filter function for a low contrast region. The generated FFT filter function is expressed as a linear sum of two functions, so that an FFT filter with a large value up to high frequencies is generated in the high spatial resolution region where the average value of projection data is small and the standard deviation is small and an FFT filter with a small value of high frequency and a large degree of smoothing is generated in the low contrast region where the X-ray absorption coefficient is large and an error of projection data is large. In addition, in all FFT filter functions, the slope (derivative) of the origin is set to the same value so that the average value of the reconstructed CT image is the same.

Next, using FIG. 17, a process in which the FFT filter generation means 253 generates an FFT filter from the feature amounts (the ROI average value $A_F$ and the standard deviation $\sigma_F$) of the projection data after convolution processing 212 calculated in the step S243 using the linear sum of the FFT filter function for a high spatial resolution region and the FFT filter function for a low contrast region will be described by way of example of the function expression which determines the content of the FFT filter function for a high spatial resolution region. The content of two input FFT filter functions (for a high spatial resolution region and a low contrast region) in the generated FFT filter is 1 in all. On the other hand, as described above, feature amounts (the ROI average value $A_F$ and the standard deviation $\sigma_F$) of the projection data are assumed to take arbitrary real values even though $A_F$ is typically a value of about 0.02/mm (X-ray absorption coefficient of water)×200 mm (body thickness)=4.0 and $\sigma_F$ is typically a value of about 0.2. By applying the same "Fermi distribution function" f(x) (definitional expression of variable x is different from Expression (1)) as Expression (1) as an example of the function whose input is an arbitrary real value and output is 0 to 1, f(x) can be set as the content of the FFT filter function for a high spatial resolution region.

[Expression 5]

$$f(x) = \frac{1}{1+e^x}, \quad x = \frac{\sigma_F - \mu_F}{\sqrt{A_F}} \cdot \beta_F \qquad (5)$$

μF is an FFT filter function threshold value input by the FFT filter input means 340, and $\beta_F$ is a filter function variation. As described previously, the value of about 10 is set as a standard value of $\beta_F$. The "Fermi distribution function" has a characteristic of f(x)+f(−x)=1. Accordingly, f(−x) can be set as the content of the FFT filter function for a low contrast region.

Hereinafter, from the same discussion as in FIG. 12 (however, definitional expression of variable x is different from Expression (1)), the solid line in FIG. 17 is the "Fermi distribution function" f(x). For the content f(x) of the FFT filter function for a high spatial resolution region, when the ROI average value $A_F$ of projection data, the filter function threshold value $\mu_F$, and the filter function variation $\beta_F$ do not change, x increases as the standard deviation $\sigma_F$ (that is, the amount of noise) of projection data increases. Accordingly, f(x) decreases. The dotted line in FIG. 17 shows changes in f(x) when the average value $A_F$ and the filter function variation $\beta_F$ are standard values $A_F$=4.0 and $\beta_F$=10 and the filter function threshold value $\mu_F$=±0.2. When the filter function threshold value $\mu_F$ is set to +0.2 at the time of $A_F$=4.0 and $\beta_F$=10, x in Expression (5) is decreased by 1.0. Accordingly, since the content f(x) of the FFT filter function for a high spatial resolution region is increased for the same standard deviation $\sigma_F$, a high resolution process is set. On the contrary, when the filter function threshold value $\mu_F$ is set to −0.2, x in Expression (5) is increased by 1.0. Accordingly, since the content f(x) of the FFT filter function for a high spatial resolution region is decreased, a low noise process is set. f(x) takes a value of about 0.73 at the time of x=−1.0, 0.5 at the time of x=0, and about 0.27 at the time of x=+1.0. FFT filter functions generated with these values are three curves illustrated in FIG. 16. This process is performed for each item of the line data, thereby generating the FFT filter conversion information formed of data in which positional information (coordinate value) of line data in the up-and-down direction (vertical direction) and the content f(x) of the FFT filter function for a high spatial resolution region match with each other. In the FFT filter conversion information, the content of the FFT filter function may be defined as a function of the coordinate value of projection data in the up-and-down direction.

(Step S246)

The filter conversion information storage means 226 stores the FFT filter conversion information calculated in step S245 (S246).

Figure 18:
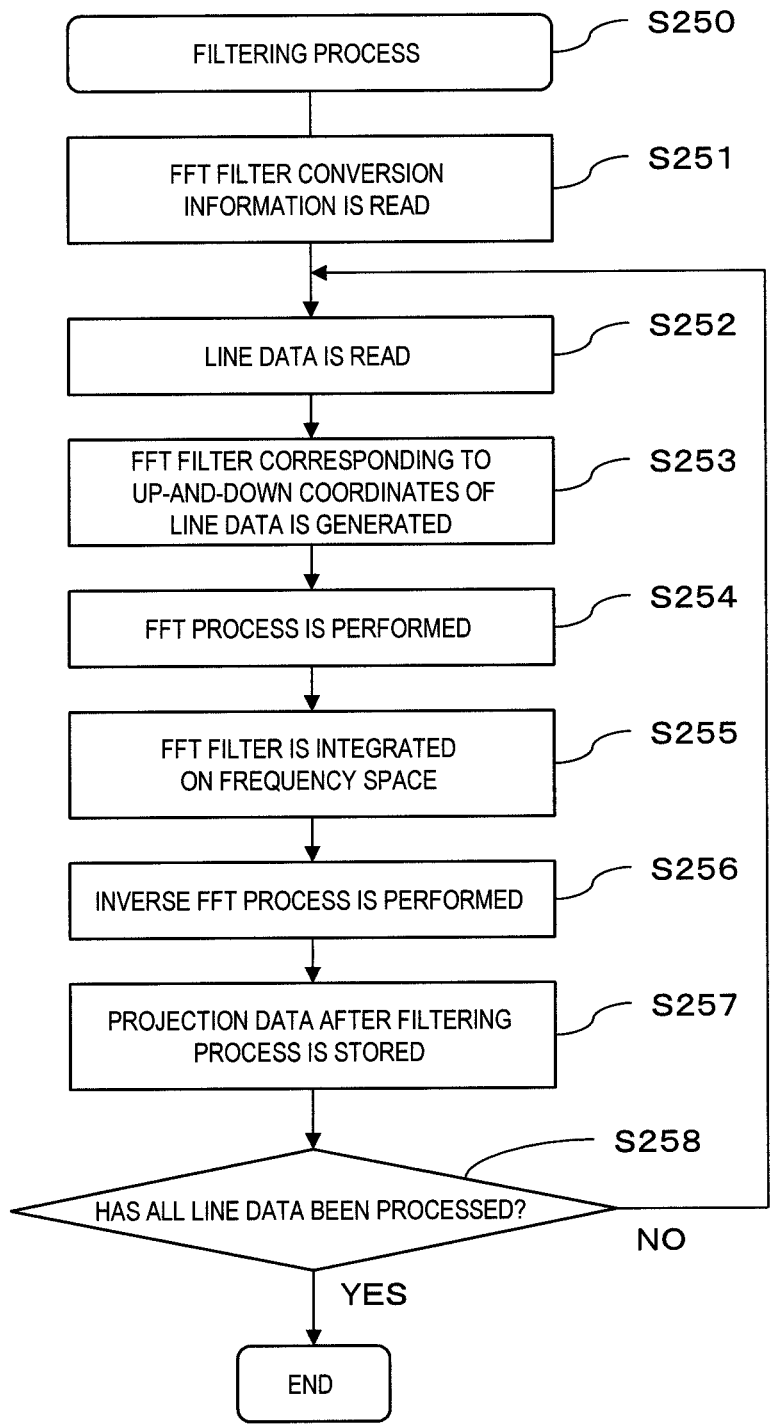
FIG. 18 is a flow chart showing the process flow of the filtering process (S250).

Next, details of the filtering process (S250) will be described using FIGS. 15 and 18. FIG. 15 is an explanatory view showing the filtering process, and FIG. 18 is a flow chart showing the process flow of the filtering process (S250). Hereinafter, the filtering process (S250) will be described along the order of steps in FIG. 18.

(Step S251)

The FFT filter conversion information reading means 251 reads the FFT filter conversion information generated by the FFT filter conversion information generation process (S240) (specifically, the FFT filter function content for a high spatial resolution region that is stored as a function of the coordinate value of projection data in the up-and-down direction in step S246) (S251).

(Step S252)

The line data reading means 252 reads horizontal line data subjected to filtering process at a time, for example, the horizontal line data 352 in FIG. 15, from the projection data after convolution processing 212 (S252).

(Step S253)

For each item of line data, the FFT filter generation means 253 generates an FFT filter corresponding to the up-and-down coordinates of the line data using the coordinate value of the line data in the up-and-down direction and the FFT filter conversion information read in step S251 (S253). The FFT filter generation means 253 calculates the FFT filter function content for a high spatial resolution region corresponding to the coordinate value of the line data in the up-and-down direction on the basis of the FFT filter conversion information. In addition, the FFT filter generation means 253 generates an FFT filter that includes the FFT filter function for a high spatial resolution region, which has been set and input by the user on the GUI screen shown in FIG. 6, according to the calculated content and includes the FFT filter function for a low contrast region, which has been similarly set and input by the user on the GUI screen shown in FIG. 6, according to the (1—above-described content) (S253).

(Step S254)

The FFT means 254 converts the horizontal line data 352 into frequency data (S254).

(Step S255)

The FFT filter integrating means 255 integrates the FFT filter generated in step S253 in the frequency data (S255).

(Step S256)

The inverse FFT means 256 converts the frequency data into projection data after filtering process in real space (S256).

(Step S257)

The filtered projection data storage means 257 stores the projection data after filtering process generated in step S256 (S257).

(Step S258)

It is determined whether or not the process of steps S252 to S257 has been executed for all of the horizontal line data. When all line data has not been processed (NO), the process returns to step S252 to execute the process of steps S252 to S257 for the subsequent line data. If YES, the filtering process (S250) ends, proceeding to the back-projection process (S260).

Although the embodiment of the present invention has been described, the configuration described above is just an example. For example, the smoothing means 230 and the convolution filter conversion information generation process (S220) may be omitted and only the FFT filter conversion information generation process and the FFT filtering process using it related to the present embodiment may be performed, or the operation process may be simplified by performing only the smoothing means 230 and the convolution filter conversion information generation process (S220). Thus, the present invention may be appropriately changed within a range not departing from the technical concept of the present invention. The former case can be realized by replacing the projection data after convolution processing 212 in the embodiment described above with the projection data 211. In addition, although the average value or the standard deviation of the pixel values in the calculation region has been used as feature amounts of the pixel value, the feature amounts are not limited to the average value or the standard deviation. For example, it is possible to use the mode or a median instead of the average value and use a dispersion instead of the standard deviation. In addition, by using values, which replace the average value and the standard deviation, as the values of the average value and the standard deviation in Expressions (1) to (5), the same operations and effects as in the embodiment described above can be achieved.

According to the present invention, by generating a convolution filter for each point of projection data, a convolution filter that changes continuously along the horizontal and vertical directions of projection data is generated. By generating an FFT filter corresponding to each item of horizontal line data of projection data or projection data after convolution processing, an FFT filter that changes continuously along the vertical direction of the projection data or the projection data after convolution processing is generated. In addition, by performing the convolution processing and the filtering process by applying these filters that change continuously, it is possible to provide an X-ray CT apparatus capable of generating an X-ray CT image with high spatial resolution by applying a sharpening filter in an imaging part, in which the average value of projection data is small and the standard deviation is small, and of generating an X-ray CT image which has low contrast and is excellent in resolution by applying a smoothing filter to suppress noise in an imaging part, in which an error of projection data is large. Therefore, improvements in the diagnostic performance in contrast imaging of the head, abdomen, and the like and orthopedic imaging of a jaw, lumbar spine, and the limbs can be expected.

In addition, for the value of projection data and the coordinate value, the convolution filter and the FFT filter whose parameters change continuously are applied. Therefore, it is possible to generate an X-ray CT image in which an unnatural boundary is not generated between a reconstruction region of a CT image with high spatial resolution and a reconstruction region of a CT image with low contrast.

REFERENCE SIGNS LIST

1: cone-beam X-ray CT apparatus
1a: C-arm type cone-beam X-ray CT apparatus mounted in a movable X-ray apparatus
2: object
3: orbital plane of rotation (midplane)
4: central axis of rotation
5: wheel
10: imaging unit
10a: imaging unit of C-arm type cone-beam X-ray CT apparatus 1a mounted in movable X-ray apparatus
11: X-ray source
11t: X-ray tube
11c: collimator
12: two-dimensional X-ray detector
13: C-type arm
14: C-type arm holder
15: ceiling support
16: ceiling rail
17: bed
18: injector
20: control operation unit
20a: control operation unit of C-arm type cone-beam X-ray CT 1a mounted in movable X-ray apparatus
24: projection of central axis of rotation 4 to two-dimensional X-ray detector 12
30: convolution filter setting screen
31: horizontal convolution filter size selection list box
32: vertical convolution filter size selection list box
33: horizontal convolution filter function threshold value setting point
34: horizontal convolution filter function variation setting point
35: vertical convolution filter function threshold value setting point
36: vertical convolution filter function variation setting point
40: FFT filter setting screen
41: head condition setting tab
42: chest condition setting tab
43: abdomen condition setting tab
44: waist condition setting tab
45: imaging part addition button
51: list box for selecting filter function for high spatial resolution region
52: list box for selecting filter function for low contrast region
53: FFT filter function threshold value setting point
54: FFT filter function variation setting point
61: pixel values of pixel, on which convolution operation is performed, surrounding pixels when size of convolution filter is 3×3
62: convolution filter of 3×3
63: pixel values of pixel, on which convolution operation is performed, surrounding pixels when size of convolution filter is 1×3
64: convolution filter of 1×3
65: pixel values of pixel, on which convolution operation is performed, surrounding pixels when size of convolution filter is 3×5
66: convolution filter of 3×5
70: information input device
80: display device
100: imaging unit control means
100a: imaging unit control means of C-arm type cone-beam X-ray CT apparatus 1a mounted in movable X-ray apparatus
101: imaging system rotation control means
102: imaging system position control means
103: X-ray irradiation control means
104: injector control means
105: bed control means
107: detection system control means
110: image collection means
111: X-ray transmission image
200: reconstruction means
210: preprocessing means,
211: projection data
212: projection data after convolution processing
220: filter conversion information generation means
221: projection data reading means
222: ROI setting means
223: feature amount calculation means
224: feature amount fitting means
225: filter conversion information calculation means
226: filter conversion information storage means
230: smoothing means
231: convolution filter conversion information reading means
232: pixel scan means
233: convolution filter generation means
234: surrounding pixel reading means
235: convolution means
236: means for storing projection data after convolution processing
238: coordinate point on projection data
239: feature amount calculation ROI
250: filtering means
251: FFT filter conversion information reading means
252: line data reading means
253: FFT filter generation means
254: FFT means
255: FFT filter integrating means
256: inverse FFT means
257: filtered projection data storage means
260: back-projection means
280: image display means
320: convolution filter input means
340: FFT filter input means
342: feature amount calculation ROI
352: horizontal line data

The invention claimed is:

1. An X-ray CT apparatus comprising:
an X-ray source that generates X-rays;
an X-ray detector that is disposed opposite the X-ray source and detects the X-ray transmitted through an object to output projection data of the object;
rotation means configured to rotate the X-ray source and the X-ray detector in a state where the X-ray source and the X-ray detector are disposed opposite each other;
filter generation means configured to generate an image processing filter that changes according to feature amounts of a pixel value included in the projection data;
reconstruction means configured to generate an X-ray CT image of the object by performing a reconstruction operation on the projection data using the generated image processing filter; and
image display means configured to display the X-ray CT image,
wherein the filter generation means generates a convolution filter for each point of the projection data as the image processing filter corresponding to feature amounts of a pixel value near the point, and
wherein the reconstruction means includes convolution means configured to superimpose the convolution filter for each point.

2. The X-ray CT apparatus according to claim 1, further comprising:
first input means configured to input generation conditions of the convolution filter; and
first filter conversion information generation means configured to generate first filter conversion information including a parameter that changes corresponding to the feature amounts of the pixel value of the projection data,
wherein the filter generation means generates the convolution filter using the input generation conditions and the first filter conversion information.

3. The X-ray CT apparatus according to claim 2,
wherein the first input means receives, as the generation conditions, inputs of a horizontal convolution size of the convolution filter, a filter function threshold value that defines a size of horizontal smoothing process, a filter function variation that defines a variation of a horizontal smoothing filter function, a vertical convolution size of the convolution filter, a filter function threshold value that defines a size of vertical smoothing process, and a filter function variation that defines a variation of a vertical smoothing filter function,
wherein the first filter conversion information generation means calculates a horizontal smoothing parameter using the feature amounts of the pixel value of the projection data, the horizontal filter function threshold value, and the horizontal filter function variation and also calculates a vertical smoothing parameter using the feature amounts of the pixel value of the projection data, the vertical filter function threshold value, and the vertical filter function variation, and
wherein the filter generation means generates the convolution filter with the input horizontal convolution size and vertical convolution size for each point of the projection data using the feature amounts of the pixel value near the point, the horizontal smoothing parameter corresponding to the feature amounts, and the vertical smoothing parameter corresponding to the feature amounts.

4. The X-ray CT apparatus according to claim 3,
wherein the first filter conversion information generation means includes first region setting means configured to set a first calculation region including each point of the projection data, first feature amount calculation means configured to calculate feature amounts of a pixel value of a pixel included in the first calculation region, and first feature amount fitting means configured to match a coordinate value of each point with the feature amounts of the pixel value, and generates the first filter conversion information in which the horizontal smoothing parameter and the vertical smoothing parameter calculated using feature amounts of a pixel value corresponding to the coordinate value is matched with the coordinate value, and
wherein the filter generation means generates the convolution filter using the coordinate value of each point of the projection data and the first filter conversion information.

5. The X-ray CT apparatus according to claim 1,
wherein for each item of line data subjected to one-dimensional Fourier transform of the projection data or projection data after convolution processing on which the convolution filter is superimposed, the filter generation means generates an FFT filter corresponding to a frequency as the image processing filter based on the feature amounts of a pixel value of the line data, and
wherein the reconstruction means includes filtering means configured to perform a filtering process using the FFT filter for each item of line data of the projection data or each item of line data of the projection data after convolution processing.

6. The X-ray CT apparatus according to claim 5, further comprising:
second input means configured to input generation conditions of the FFT filter; and
second filter conversion information generation means configured to generate second filter conversion information including a parameter that changes corresponding to the feature amounts of the pixel value of line data of the projection data,
wherein the filter generation means generates the FFT filter for each item of line data of the projection data or each item of line data of the projection data after convolution processing using the input generation conditions and the second filter conversion information.

7. The X-ray CT apparatus according to claim 6,
wherein the second filter conversion information generation means includes second region setting means configured to set a second calculation region including line data of the projection data or the projection data after convolution processing, second feature amount calculation means configured to calculate feature amounts of a pixel value of a pixel included in the second calculation region, and second feature amount fitting means configured to match a coordinate value in a direction perpendicular to a longitudinal direction of the line data with the feature amounts of the pixel value, and generates second filter conversion information in which a parameter calculated using feature amounts of a pixel value corresponding to the coordinate value is matched with the coordinate value, and
wherein the filter generation means generates the FFT filter using the coordinate value of each item of the line data and the second filter conversion information.

8. The X-ray CT apparatus according to claim 7,
wherein the second input means receives, as the generation conditions, inputs of a first filter function used in a region with relatively high spatial resolution, a second filter function used in a region with relatively low contrast, a filter function threshold value that defines a size of a content of the first or second filter function, and a filter function variation indicating a variation of the content, wherein the second filter conversion information generation means calculates the parameter from the content corresponding to the feature amounts of the pixel value of the second calculation region, and wherein the filter generation means generates the FFT filter by calculating the content of the first or second filter function of each item of the line data on the basis of the second filter conversion information and integrating the first and second filter functions according to the content.

9. A control method of an X-ray CT apparatus including an X-ray source that generates X-rays, an X-ray detector that is disposed opposite the X-ray source and detects the X-ray transmitted through an object to output projection data of the object, and rotation means configured to rotate the X-ray source and the X-ray detector in a state where the X-ray source and the X-ray detector are disposed opposite each other, the control method comprising:

a step of generating an image processing filter that changes according to feature amounts of a pixel value included in the projection data;

a step of generating an X-ray CT image of the object by performing a reconstruction operation on the projection data using the generated image processing filter;

a step of displaying the X-ray CT image;

a step of generating a convolution filter for each point of the projection data as the image processing filter corresponding to feature amounts of a pixel value near the point; and a step of superimposing the convolution filter for each point.

10. The control method of claim 9, further comprising:

a step of generating, for each item of line data subjected to one-dimensional Fourier transform of the projection data or projection data after convolution processing on which the convolution filter is superimposed, an FFT filter corresponding to a frequency as the image processing filter on the basis of feature amounts of a pixel value of the line data; and a step of performing a filtering process using the FFT filter for each item of line data of the projection data or each item of line data of the projection data after convolution processing.

* * * * *